(12) United States Patent
Lee et al.

(10) Patent No.: US 9,605,205 B2
(45) Date of Patent: Mar. 28, 2017

(54) LIQUID CRYSTAL COMPOSITION AND LIQUID CRYSTAL DISPLAY INCLUDING THE SAME

(71) Applicant: Samsung Display Co., Ltd., Yongin-si, Gyeonggi-do (KR)

(72) Inventors: Kyung Hee Lee, Suwon-si (KR); Sun Young Kwon, Seoul (KR); Ji Hong Bae, Yongin-si (KR); Keun Chan Oh, Cheonan-si (KR)

(73) Assignee: SAMSUNG DISPLAY CO., LTD., Gyeonggi-do (KR)

( * ) Notice: Subject to any disclaimer, the term of this patent is extended or adjusted under 35 U.S.C. 154(b) by 0 days.

(21) Appl. No.: 15/073,198

(22) Filed: Mar. 17, 2016

(65) Prior Publication Data

US 2017/0029699 A1 Feb. 2, 2017

(30) Foreign Application Priority Data

Jul. 31, 2015 (KR) ........................ 10-2015-0109082

(51) Int. Cl.
| | |
|---|---|
| *G02F 1/1333* | (2006.01) |
| *C09K 19/30* | (2006.01) |
| *C07C 43/184* | (2006.01) |
| *C07C 25/24* | (2006.01) |
| *C07C 43/225* | (2006.01) |
| *C07C 43/247* | (2006.01) |
| *C07C 43/192* | (2006.01) |
| *C07C 13/28* | (2006.01) |

(52) U.S. Cl.
CPC .......... *C09K 19/3001* (2013.01); *C07C 13/28* (2013.01); *C07C 25/24* (2013.01); *C07C 43/184* (2013.01); *C07C 43/192* (2013.01); *C07C 43/225* (2013.01); *C07C 43/247* (2013.01); *C07C 2101/14* (2013.01)

(58) Field of Classification Search
CPC . C09K 19/3001; G02F 1/1333; C07C 43/184; C07C 43/225; C07C 43/247; C07C 43/192; C07C 25/24; C07C 13/28; C07C 2101/14
USPC ......................... 252/299.01, 299.6; 349/182
See application file for complete search history.

(56) References Cited

U.S. PATENT DOCUMENTS

| | | |
|---|---|---|
| 5,965,060 A | 10/1999 | Tarumi et al. |
| 7,731,865 B2 | 6/2010 | Bernatz et al. |

FOREIGN PATENT DOCUMENTS

| | | |
|---|---|---|
| KR | 100716969 | 5/2007 |
| KR | 1020130110162 | 10/2013 |
| KR | 1020140014177 | 2/2014 |

*Primary Examiner* — Geraldina Visconti
(74) *Attorney, Agent, or Firm* — Cantor Colburn LLP

(57) ABSTRACT

A liquid crystal composition includes one or more compounds represented by Chemical Formula 1:

Chemical Formula 1

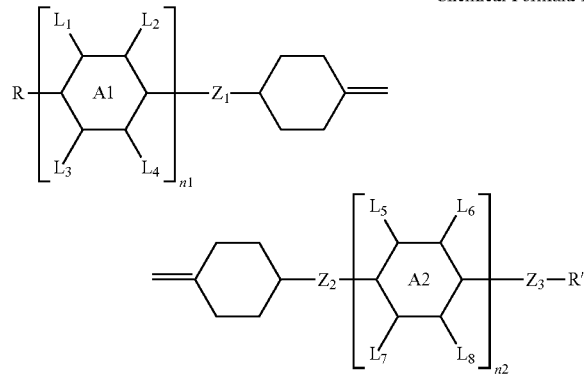

wherein in Chemical Formula 1, A1, A2, $L_1$ to $L_8$, R, R', $Z_1$ to $Z_3$, n1, and n2 are the same as described in the specification.

20 Claims, 4 Drawing Sheets

LIQUID CRYSTAL COMPOSITION AND LIQUID CRYSTAL DISPLAY INCLUDING THE SAME

This application claims priority to and the benefit of Korean Patent Application No. 10-2015-0109082 filed in the Korean Intellectual Property Office on Jul. 31, 2015, the content of which is incorporated herein in its entirety by reference.

BACKGROUND (a) Technical Field

The present inventive concept relates to a liquid crystal composition and a liquid crystal display (LCD) including the liquid crystal composition.

(b) Description of the Related Art

Liquid crystal displays are now one of the most widely used flat panel displays.

The liquid crystal display determines a direction of the liquid crystal molecules of the liquid crystal layer and controls transmittance of light passing through the liquid crystal layer by applying a voltage to the field generating electrodes to generate an electric field in the liquid crystal layer.

The liquid crystal composition is very important for the liquid crystal display to achieve a desired image by controlling the transmittance of light. In particular, various uses of liquid crystal displays require various characteristics, such as, low-voltage driving, a high voltage holding ratio (VHR), a wide viewing angle, a wide operation temperature range, and high-speed response.

In order to obtain a high speed response characteristic for a liquid crystal display, research is being conducted to improve the physical properties, such as a rotation viscosity, a refractive index, and an elastic coefficient included in the liquid crystal composition.

Thus, there remains a need for a liquid crystal display device including, capable of realizing high speed response characteristics and low temperature stability.

The above information disclosed in this Background section is only to enhance the understanding of the background of the invention, and therefore, it may contain information that does not form the prior art that is already known in this country or anywhere in the world to a person of ordinary skill in the art.

SUMMARY

The present disclosure has been made in an effort to provide a liquid crystal composition and a display device including the same, capable of realizing high speed response characteristics and low temperature stability.

A liquid crystal composition according to an exemplary embodiment includes one or more compounds represented by Chemical Formula 1.

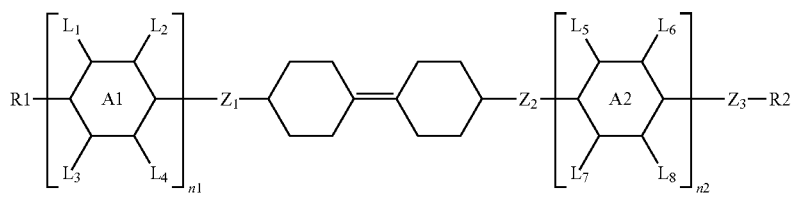

Chemical Formula 1

In Chemical Formula 1,

and

are independently one or more selected from,

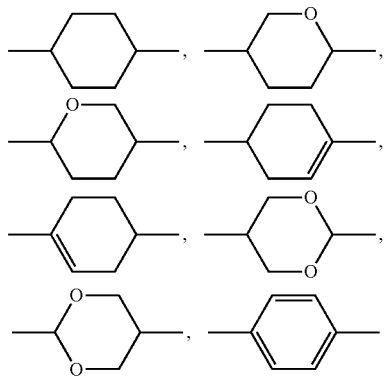

$L_1$ to $L_8$ are independently —H, —F, —Cl, —OCF$_3$, —CF$_3$, —CH$_2$F or —CHF$_2$, $Z_1$, $Z_2$ and $Z_3$ are independently a single bond, —COO—, —OCO—, —CF$_2$O—, —OCF$_2$—, —CH$_2$O, —OCH$_2$—, —SCH$_2$—, —CH$_2$S—, —CH$_2$CH$_2$—, —C$_2$F$_4$—, —CH$_2$CF$_2$—, —CF$_2$CH$_2$—, —(CH$_2$)$_z$— (wherein z is an integer of 0 to 10), —CH=CH—, —CF=CF—, —CH=CF—, —CF=CH—, —C≡C— or —CH=CHCH$_2$O—, and R1 and R2 are independently hydrogen, halogen, cyano, a C1 to C5 alkyl, a C2 to C5 alkenyl, a C1 to C5 alkoxy, and $n_1$ and $n_2$ are independently integers of 0 to 3, provided that the sum of $n_1$ and $n_2$ is more than 1.

In Chemical Formula 1,
R1 is a C1 to C5 alkyl and R2 is a C1 to C5 alkyl,
R1 is a C1 to C5 alkyl and R2 is a C2 to C5 alkenyl, or
R1 is a C1 to C5 alkyl and R2 is a C1 to C5 alkoxy.

The compound represented by Chemical Formula 1 includes one or more selected from the compounds represented by Chemical Formula 1-1 to Chemical Formula 1-16.

Chemical Formula 1-1

Chemical Formula 1-2

Chemical Formula 1-3

Chemical Formula 1-4

Chemical Formula 1-5

Chemical Formula 1-6

Chemical Formula 1-7

Chemical Formula 1-8

Chemical Formula 1-9

Chemical Formula 1-10

Chemical Formula 1-11

Chemical Formula 1-12

Chemical Formula 1-13

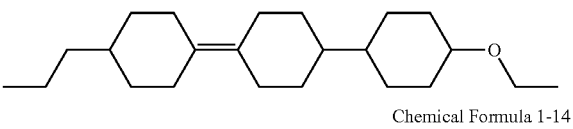

Chemical Formula 1-14

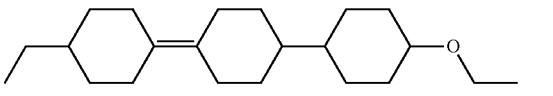

Chemical Formula 1-15

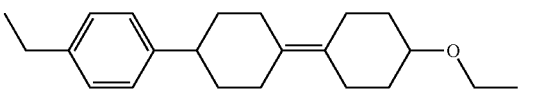

Chemical Formula 1-16

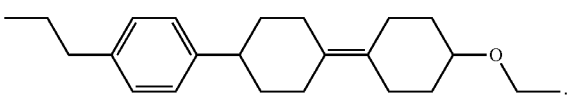

The compound represented by Chemical Formula 1 includes one or more selected from compounds represented by Chemical Formula 1-17 to Chemical Formula 1-29.

Chemical Formula 1-17

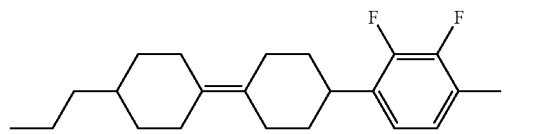

Chemical Formula 1-18

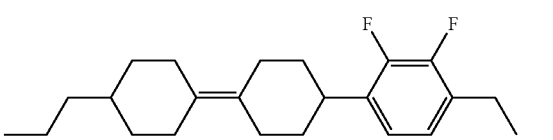

Chemical Formula 1-19

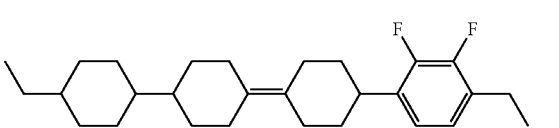

Chemical Formula 1-20

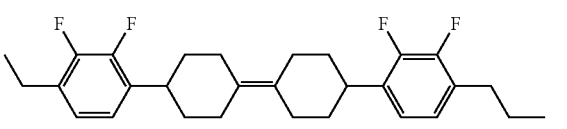

Chemical Formula 1-21

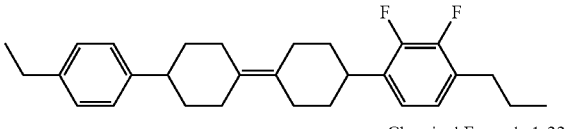

Chemical Formula 1-22

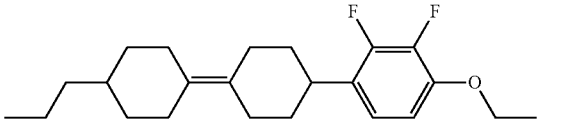

Chemical Formula 1-23

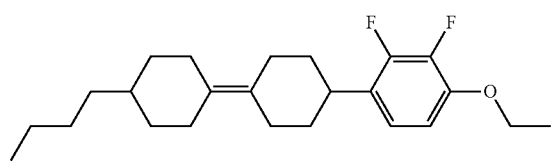

Chemical Formula 24

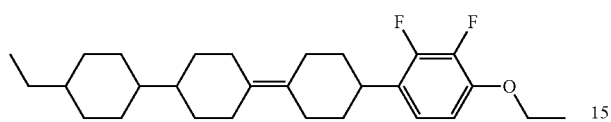

Chemical Formula 25

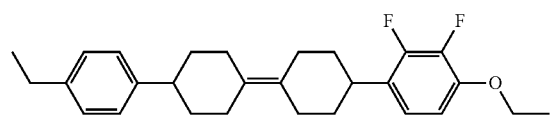

Chemical Formula 26

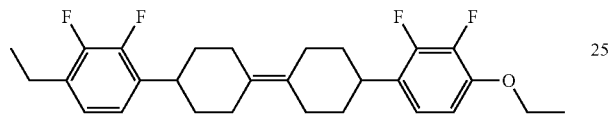

Chemical Formula 27

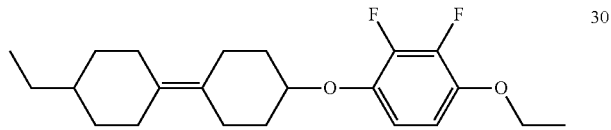

Chemical Formula 28

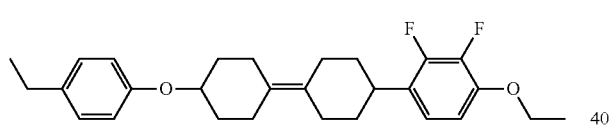

Chemical Formula 29

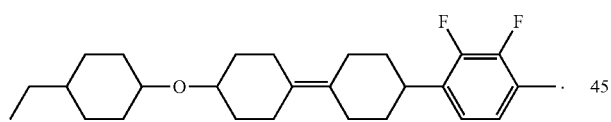

An amount of the compound represented by Chemical Formula 1 is in a range of about 0.10 percent by weight to about 60 percent by weight based on 100 percent by weight of the liquid crystal composition.

The liquid crystal composition includes one or more compounds selected from Chemical Formula 2 to Chemical Formula 20.

Chemical Formula 2

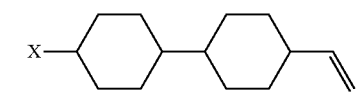

Chemical Formula 3

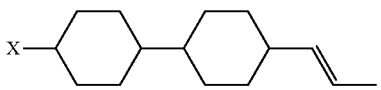

Chemical Formula 4

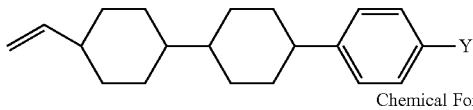

Chemical Formula 5

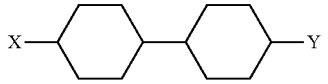

Chemical Formula 6

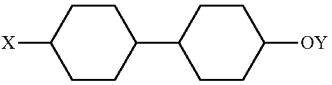

Chemical Formula 7

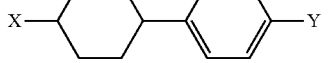

Chemical Formula 8

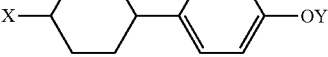

Chemical Formula 9

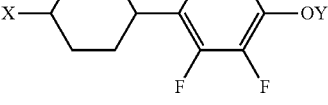

Chemical Formula 10

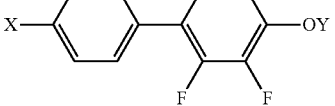

Chemical Formula 11

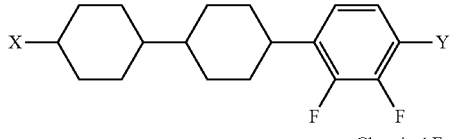

Chemical Formula 12

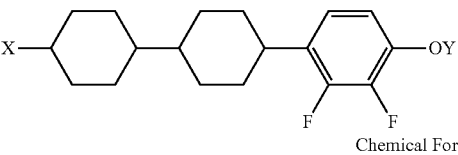

Chemical Formula 13

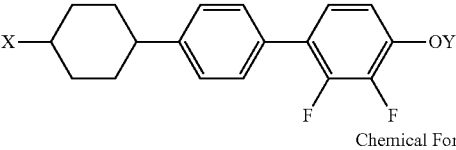

Chemical Formula 14

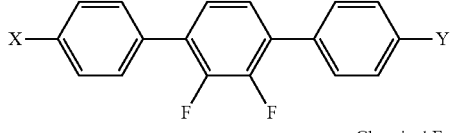

Chemical Formula 15

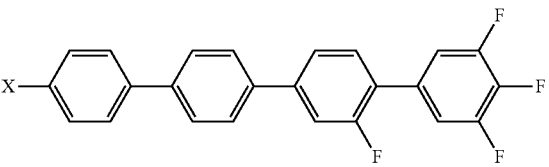

Chemical Formula 16
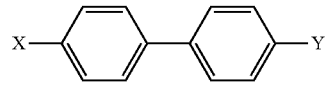

Chemical Formula 17
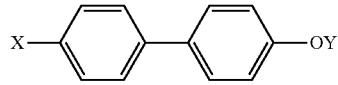

Chemical Formula 18
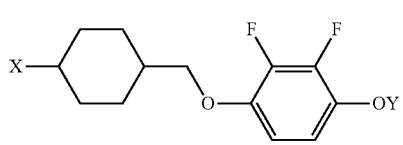

Chemical Formula 19
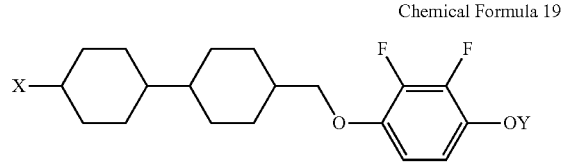

Chemical Formula 20
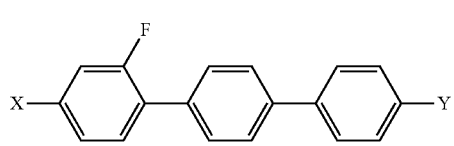

In Chemical Formula 2 to Chemical Formula 20, X and Y are independently $C_nH_{2n+1}$, wherein n is 1 to 5.

An amount of Chemical Formula 2 to Chemical Formula 20 is in a range of about 1 percent by weight to about 30 percent by weight based on 100 percent by weight of the entire liquid crystal composition.

The compound represented by Chemical Formula 1 is the compound represented by Chemical Formula 17, wherein the liquid crystal composition includes two or more, preferably all of the compounds represented by Chemical Formula 31 to Chemical Formula 36.

Chemical Formula 1-17
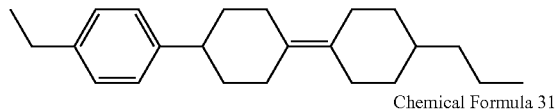

Chemical Formula 31
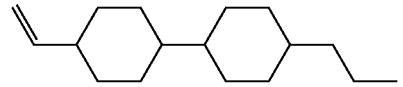

Chemical Formula 32
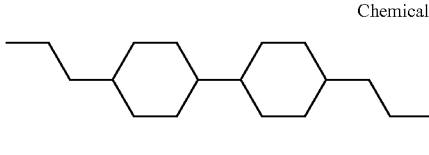

Chemical Formula 33
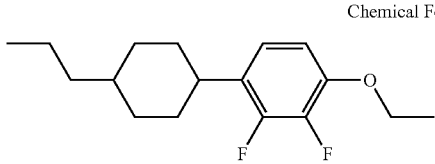

Chemical Formula 34
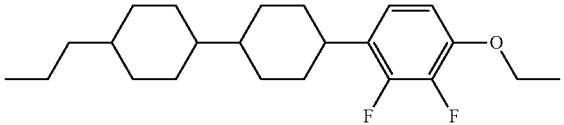

Chemical Formula 35
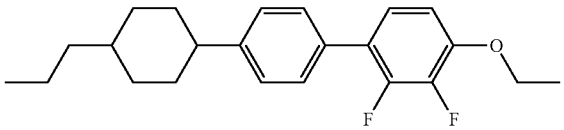

Chemical Formula 36

The compound represented by Chemical Formula 1 is the compound represented by Chemical Formula 18, wherein the liquid crystal composition includes the compounds represented by Chemical Formula 31 to Chemical Formula 33, Chemical Formula 35, and Chemical Formula 36.

Chemical Formula 1-18
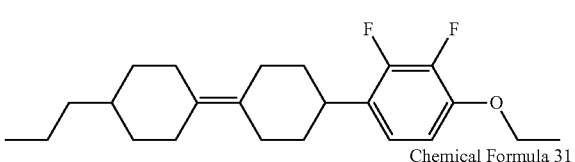

Chemical Formula 31
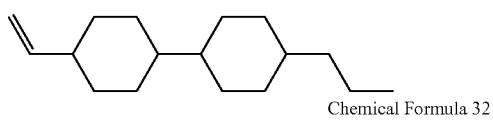

Chemical Formula 32
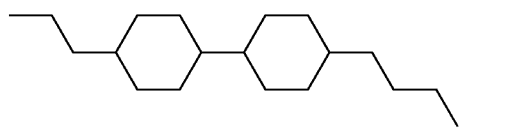

Chemical Formula 33
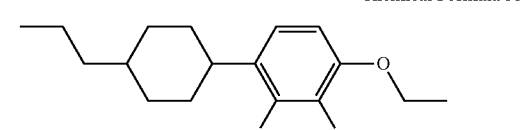

Chemical Formula 35
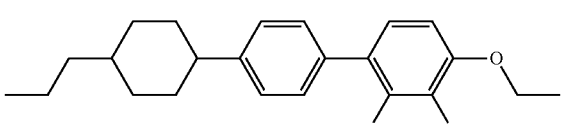

Chemical Formula 36
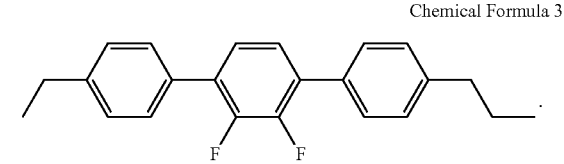

The liquid crystal composition further includes a reactive mesogen.

A liquid crystal display according to an exemplary embodiment includes:

a first insulation substrate formed with a pixel electrode;

a second insulation substrate facing the first insulation substrate; and a liquid crystal layer positioned between the first insulation substrate and the second insulation substrate, wherein the liquid crystal layer includes one or more compounds represented by Chemical Formula 1.

$n_1$ and $n_2$ are independently integers of 0 to 3, wherein the sum of $n_1$ and $n_2$ is more than 1.

In the compound represented by Chemical Formula 1,

R1 is a C1 to C5 alkyl and R2 is a C1 to C5 alkyl,

R1 is a C1 to C5 alkyl and R2 is a C2 to C5 alkenyl, or

R1 is a C1 to C5 alkyl and R2 is a C1 to C5 alkoxy.

The compound represented by Chemical Formula 1 includes one or more selected from compounds represented by Chemical Formula 1-1 to Chemical Formula 1-16.

Chemical Formula 1

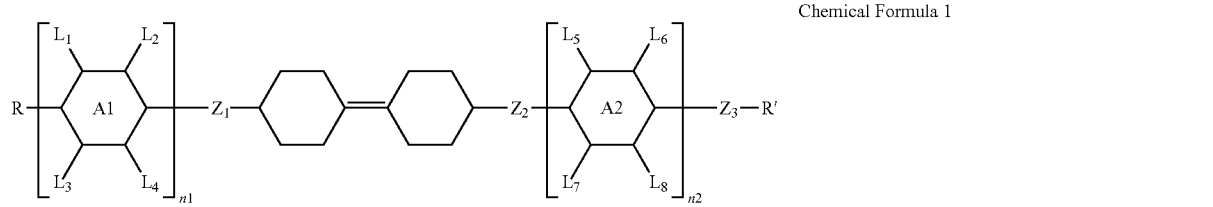

In Chemical Formula 1,

and

are independently one or more selected from,

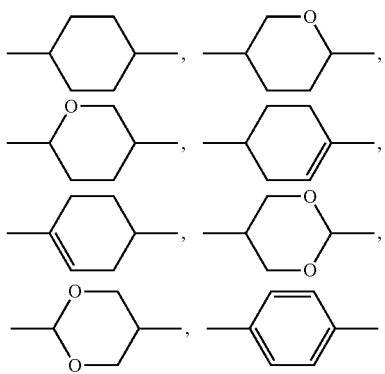

$L_1$ to $L_8$ are independently —H, —F, —Cl, —OCF$_3$, —CF$_3$, —CH$_2$F or —CHF$_2$, $Z_1$, $Z_2$ and $Z_3$ are independently a single bond, —COO—, —OCO—, —CF$_2$O—, —OCF$_2$—, —CH$_2$O, —OCH$_2$—, —SCH$_2$—, —CH$_2$S—, —CH$_2$CH$_2$—, —C$_2$F$_4$—, —CH$_2$CF$_2$—, —CF$_2$CH$_2$—, —(CH$_2$)$_z$— (wherein z is an integer of 0 to 10), —CH═CH—, —CF═CF—, —CH═CF—, —CF═CH—, —C≡C— or —CH═CHCH$_2$O—, R1 and R2 are independently hydrogen, halogen, cyano, a C1 to C5 alkyl, a C2 to C5 alkenyl, a C1 to C5 alkoxy, and Chemical Formula 1-1

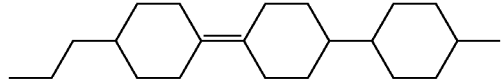

Chemical Formula 1-2

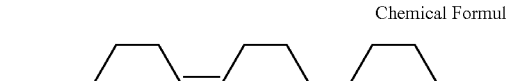

Chemical Formula 1-3

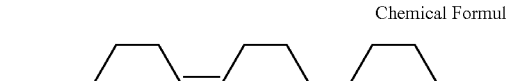

Chemical Formula 1-4

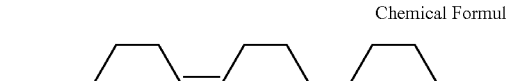

Chemical Formula 1-5

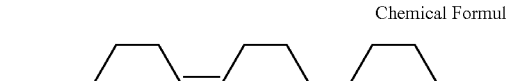

Chemical Formula 1-6

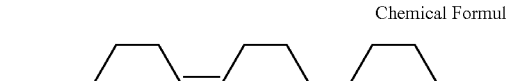

Chemical Formula 1-7

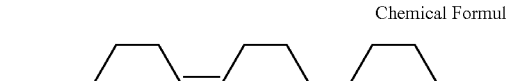

Chemical Formula 1-8

Chemical Formula 1-9

Chemical Formula 1-10
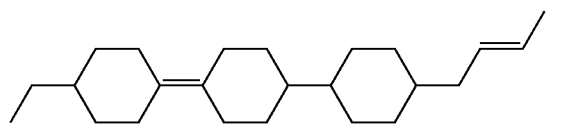

Chemical Formula 1-11
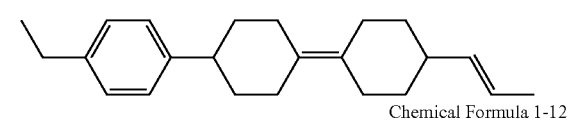

Chemical Formula 1-12
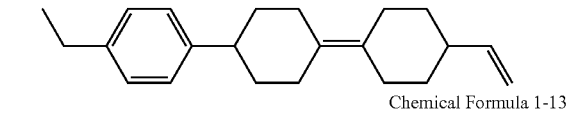

Chemical Formula 1-13
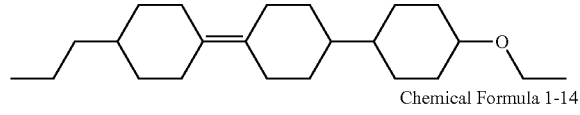

Chemical Formula 1-14
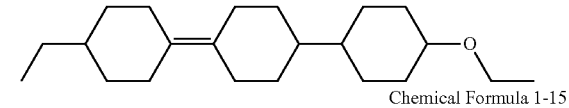

Chemical Formula 1-15
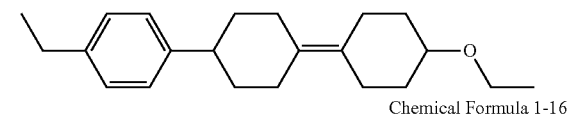

Chemical Formula 1-16
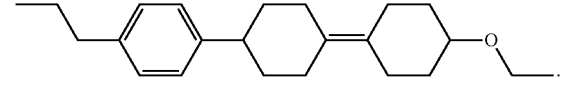

The compound represented by Chemical Formula 1 includes one or more selected from compounds represented by Chemical Formula 1-17 to Chemical Formula 1-29.

Chemical Formula 1-17
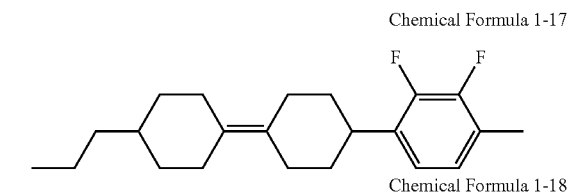

Chemical Formula 1-18
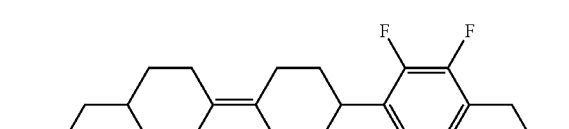

Chemical Formula 1-19
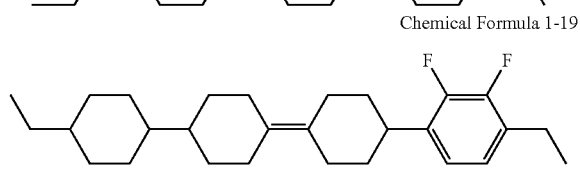

Chemical Formula 1-20
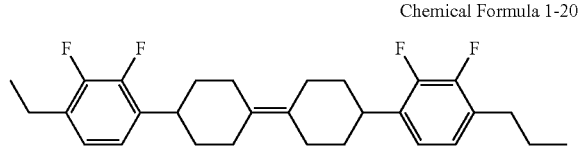

Chemical Formula 1-21
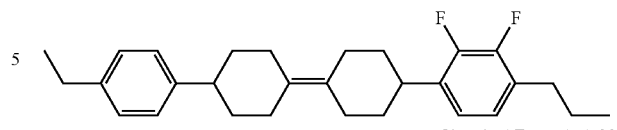

Chemical Formula 1-22
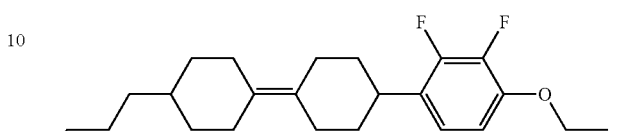

Chemical Formula 1-23
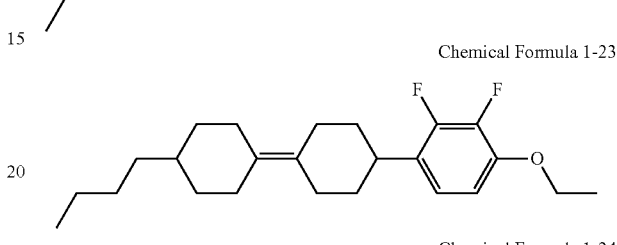

Chemical Formula 1-24
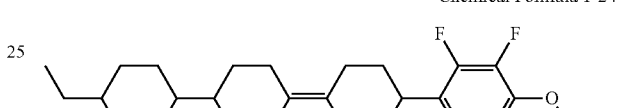

Chemical Formula 1-25
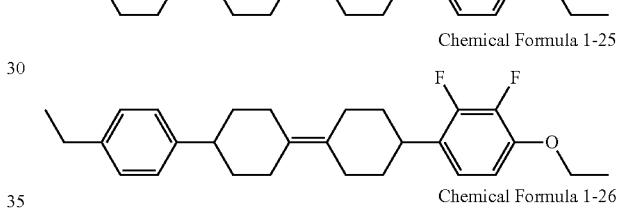

Chemical Formula 1-26
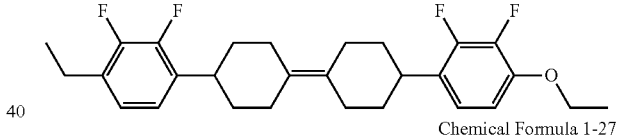

Chemical Formula 1-27
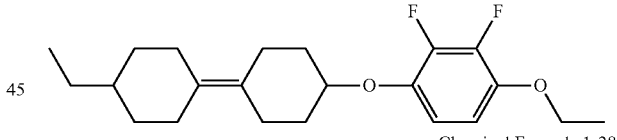

Chemical Formula 1-28
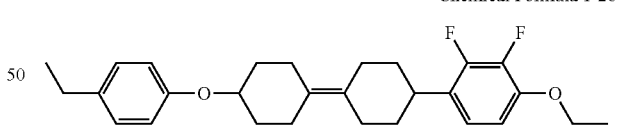

Chemical Formula 1-29
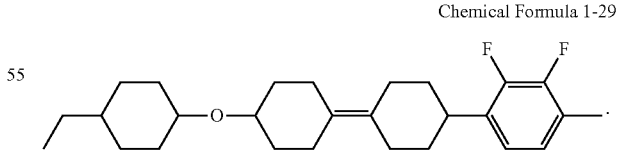

An amount of the compound represented by Chemical Formula 1 is in a range of about 0.1 percent by weight to about 60 percent by weight based on 100 percent by weight of the liquid crystal composition.

The liquid crystal composition includes one or more compounds selected from Chemical Formula 2 to Chemical Formula 20.

In Chemical Formula 2 to Chemical Formula 20, X and Y are independently $C_nH_{2n+1}$, wherein n is 1 to 5.

An amount of Chemical Formula 2 to Chemical Formula 20 is in a range of about 1 percent by weight to about 30 percent by weight based on 100 percent by weight of the entire liquid crystal composition.

The compound represented by Chemical Formula 1 is the compound represented by Chemical Formula 1-17, wherein the liquid crystal composition includes at least two of the compounds represented by Chemical Formula 31 to Chemical Formula 36.

Chemical Formula 32
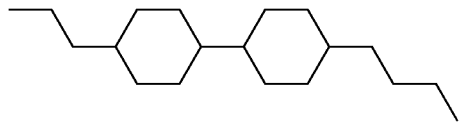 [SMILES: CCCCC1CCC(C2CCC(CCC)CC2)CC1]

Chemical Formula 33
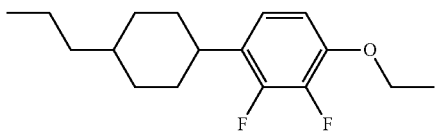 [SMILES: CCCC1CCC(c2ccc(OCC)c(F)c2F)CC1]

Chemical Formula 34
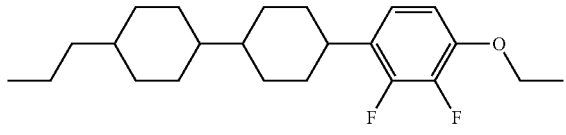 [SMILES: CCCC1CCC(C2CCC(c3ccc(OCC)c(F)c3F)CC2)CC1]

Chemical Formula 35
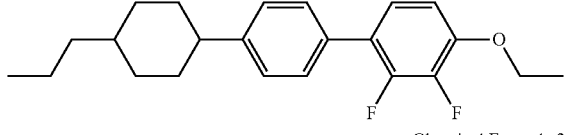

Chemical Formula 36
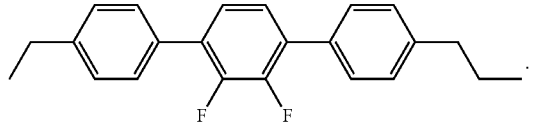

The compound represented by Chemical Formula 1 is the compound represented by Chemical Formula 1-18, wherein the liquid crystal composition includes comprises at least two preferably all, of the compounds represented by Chemical Formula 31 to Chemical Formula 33, Chemical Formula 35, and Chemical Formula 36.

Chemical Formula 1-18
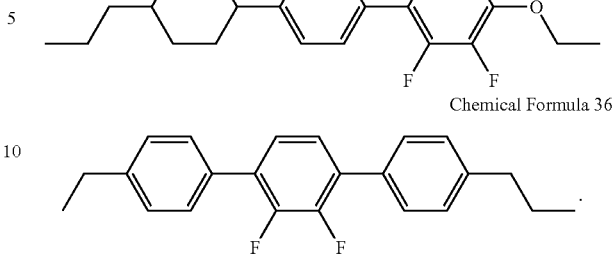

Chemical Formula 31
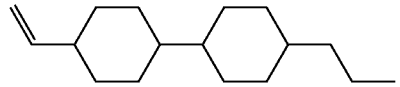 [SMILES: C=CC1CCC(C2CCC(CCC)CC2)CC1]

Chemical Formula 32
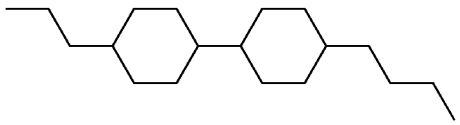 [SMILES: CCCCC1CCC(C2CCC(CCC)CC2)CC1]

Chemical Formula 33
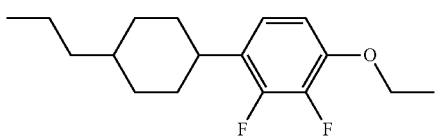

Chemical Formula 35
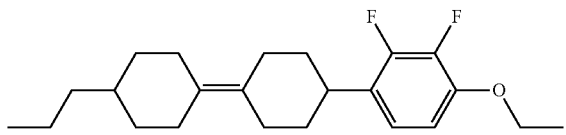

Chemical Formula 36
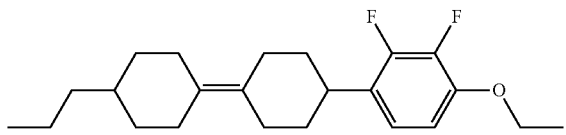

The liquid crystal layer further includes a reactive mesogen.

As stated above, an exemplary embodiment provides a liquid crystal composition including a compound that is cyclohexane connected by a double bond, which when applied to form a liquid crystal display can improve the performance of the liquid crystal display.

BRIEF DESCRIPTION OF THE DRAWINGS

The above and other aspects, advantages, and features of this disclosure will become more apparent by describing in further detail exemplary embodiments thereof with reference to the accompanying drawings, in which.

DETAILED DESCRIPTION OF THE EMBODIMENTS

Figure 1:
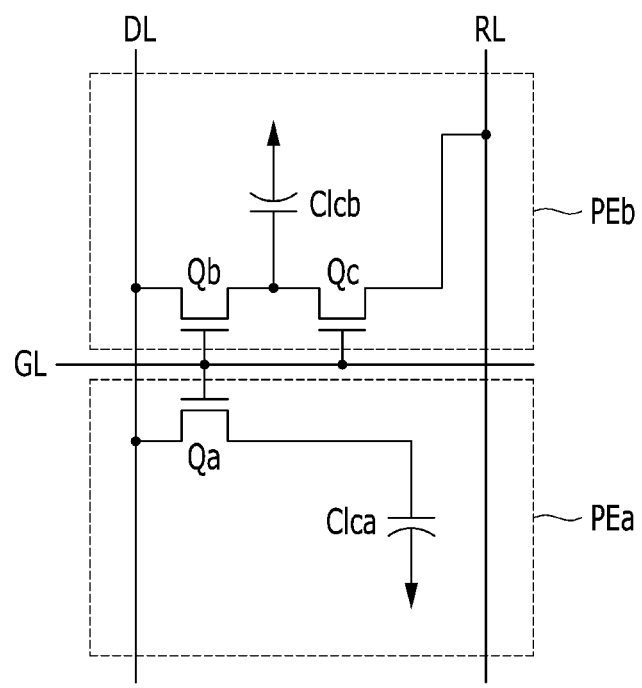
FIG. 1 is an equivalent circuit diagram for one pixel of the liquid crystal display according to the exemplary embodiment.

The present inventive concept will be described more fully hereinafter with reference to the accompanying drawings, in which exemplary embodiments of the invention are shown. Reference will be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Rather, these embodiments are provided so that this disclosure will be thorough and complete, and will fully convey the effects and features of the present disclosure and ways to implement the present disclosure will fully convey the concept of the invention to those skilled in the art. Accordingly, the exemplary embodiments are merely described below, by referring to the figures, to explain aspects. As those skilled in the art would realize, the described embodiments may be modified in various different ways, all without departing from the spirit or scope of the present disclosure. As used herein, the term "and/or" includes any and all combinations of one or more of the associated listed items. Expressions such as "at least one of,"

when preceding a list of elements, modify the entire list of elements and do not modify the individual elements of the list.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims. In the drawings, like reference numerals denote like elements throughout, and thus redundant description thereof will be omitted.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

As used herein, the terms such as "comprising", "including", "having", or the like are intended to indicate the existence of the features regions, integers, steps, operations, components, and/or elements disclosed in the specification, and are not intended to preclude the possibility that one or more other features or elements may exist or may be added.

In the drawings, the thickness of layers, films, panels, regions, etc., are exaggerated for clarity. The size or thickness of each element shown in the drawings are arbitrarily illustrated for better understanding or ease of description, and thus the present disclosure is not limited thereto.

Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Hereinafter, a liquid crystal composition according to an exemplary embodiment, and a liquid crystal display including the liquid crystal display, will be described in detail with reference to the accompanying drawings.

A liquid crystal composition according to an exemplary embodiment includes one or more of the compound represented by Chemical Formula 1.

Chemical Formula 1

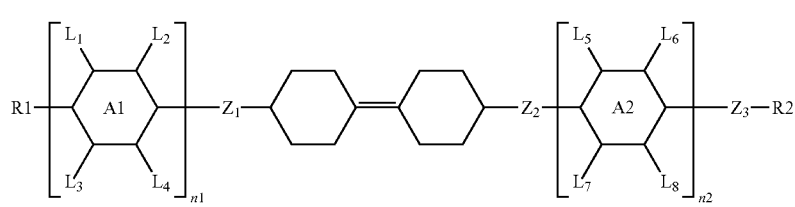

In Chemical Formula 1,

and

are independently one or more selected from

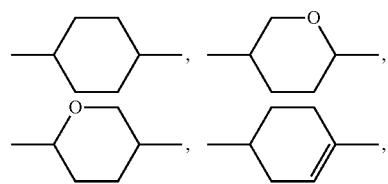

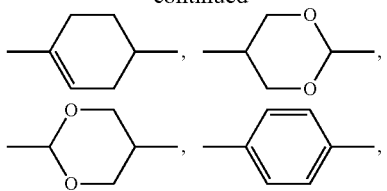

$L_1$ to $L_8$ are independently —H, —F, —Cl, —OCF$_3$, —CF$_3$, —CH$_2$F or —CHF$_2$, $Z_1$, $Z_2$ and $Z_3$ are independently a single bond, —COO—, —OCO—, —CF$_2$O—, —OCF$_2$—, —CH$_2$O, —OCH$_2$—, —SCH$_2$—, —CH$_2$S—, —CH$_2$CH$_2$—, —C$_2$F$_4$—, —CH$_2$CF$_2$—, —CF$_2$CH$_2$—, —(CH$_2$)$_z$— (wherein z is an integer of 0 to 10), —CH=CH—, —CF=CF—, —CH=CF—, —CF=CH—, —C≡C— or —CH=CHCH$_2$O—, R1 and R2 are independently hydrogen, halogen, cyano, a C1 to C5 alkyl, a C2 to C5 alkenyl, a C1 to C5 alkoxy, and $n_1$ and $n_2$ are independently integers of 0 to 3, wherein the sum of n1 and n2 is more than 1.

A schematic view of the manufacturing process of the compound represented by Chemical Formula 1 may be as follows:

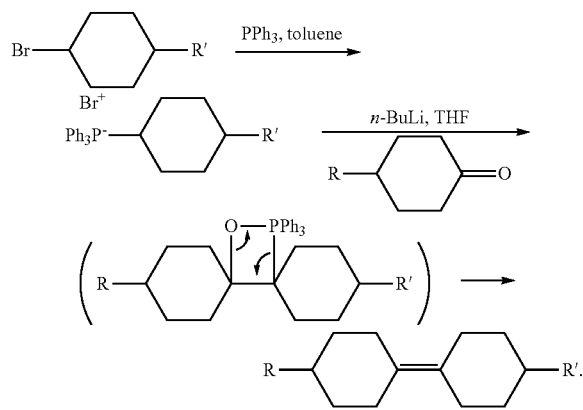

That is, after synthesizing a cyclohexane connected by double bond using the above manufacturing process, the compound is synthesized in the position of R and R' using a prior art manufacturing method, whereby the compound represented by Chemical Formula 1 is manufactured.

Also, in another manufacturing process, the cyclohexane compound represented by Chemical Formula 1 is formed at the position of R and R'.

However, the manufacturing process is an exemplary embodiment, and the compound represented by Chemical Formula 1 may be synthesized by another manufacturing process.

In the compound represented by Chemical Formula 1,

R1 may be a C1 to C5 alkyl and R2 may be C1 to C5 alkyl,

R1 may be a C1 to C5 alkyl and R2 may be a C2 to C5 alkenyl, or

R1 may be a C1 to C5 alkyl and R2 may be a C1 to C5 alkoxy, but it is not limited thereto.

The compound represented by Chemical Formula 1 may include one or more selected from the compounds represented by Chemical Formula 1-1 to Chemical Formula 1-16.

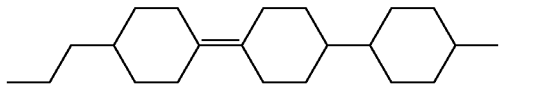

Chemical Formula 1-1

Chemical Formula 1-2

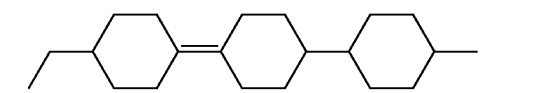

Chemical Formula 1-3

Chemical Formula 1-4

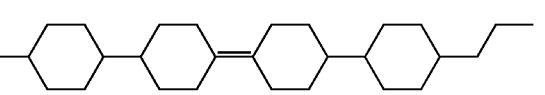

Chemical Formula 1-5

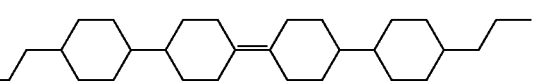

Chemical Formula 1-6

Chemical Formula 1-7

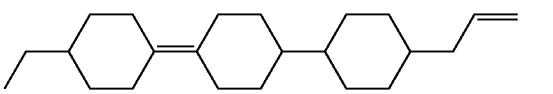

Chemical Formula 1-8

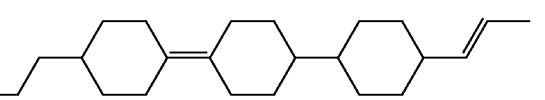

Chemical Formula 1-9

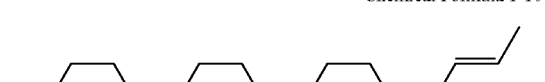

Chemical Formula 1-10

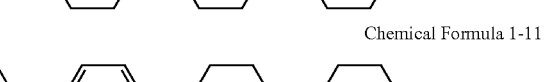

Chemical Formula 1-11

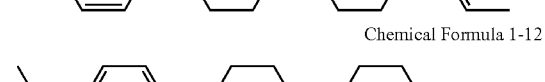

Chemical Formula 1-12

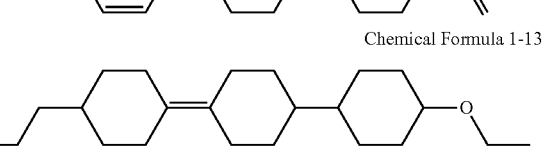

Chemical Formula 1-13

Chemical Formula 1-14
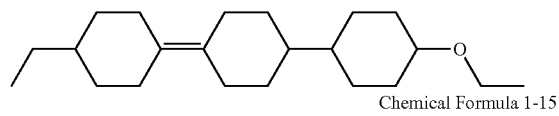

Chemical Formula 1-15
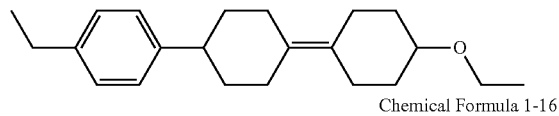

Chemical Formula 1-16
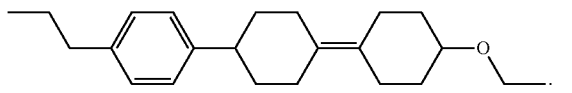

Or, the compound represented by Chemical Formula 1 may include one or more selected from the compounds represented by Chemical Formula 1-17 to Chemical Formula 1-29.

Chemical Formula 1-17
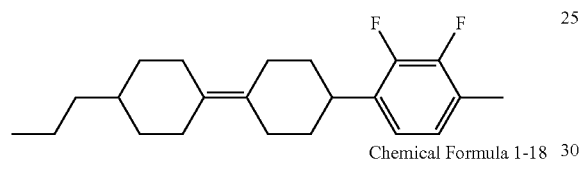

Chemical Formula 1-18
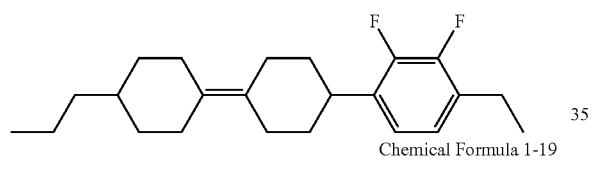

Chemical Formula 1-19
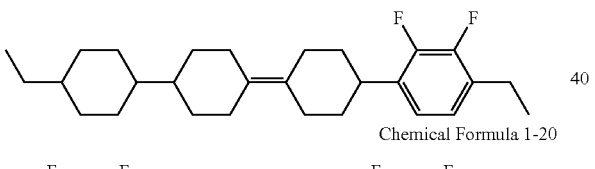

Chemical Formula 1-20
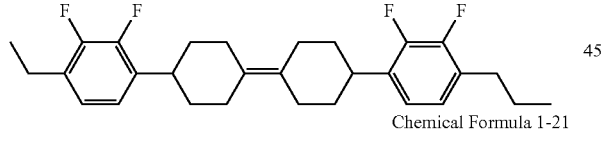

Chemical Formula 1-21
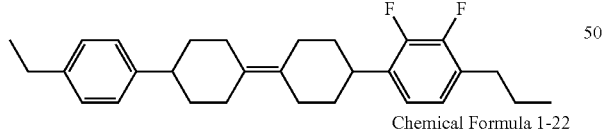

Chemical Formula 1-22
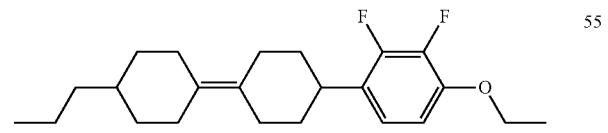

Chemical Formula 1-23
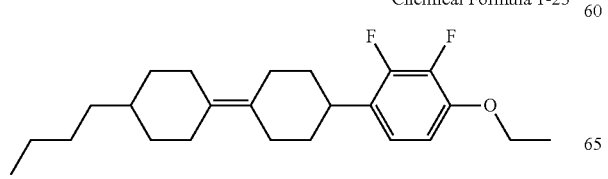

Chemical Formula 24
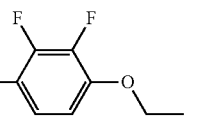

Chemical Formula 25
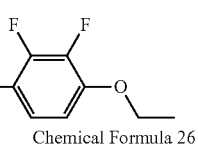

Chemical Formula 26
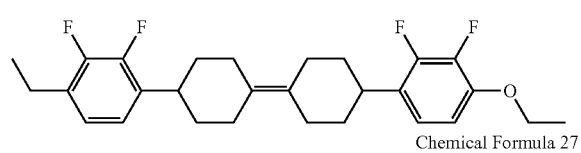

Chemical Formula 27
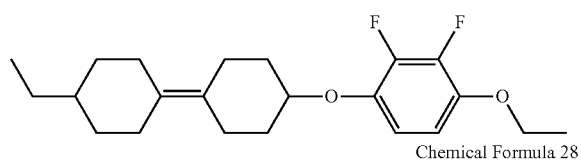

Chemical Formula 28

Chemical Formula 29

The liquid crystal composition according to an exemplary embodiment may include the compounds represented by Chemical Formula 1 in a range about 0.1 percent by weight (wt %) to about 60 wt % based no 100 wt % of the liquid crystal composition.

Also, the liquid crystal composition according to an exemplary embodiment may further include one or more compounds selected from the compounds represented by Chemical Formula 2 to Chemical Formula 20.

Chemical Formula 2
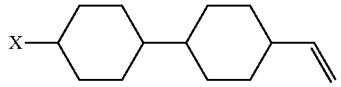

Chemical Formula 3
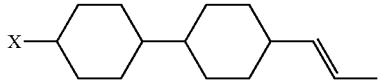

Chemical Formula 4
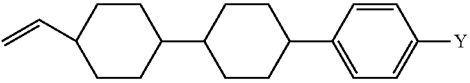

Chemical Formula 5
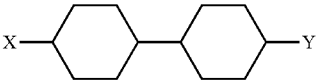

Chemical Formula 6
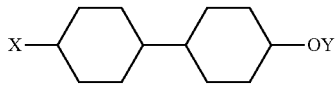

Chemical Formula 7
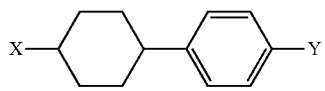

Chemical Formula 8
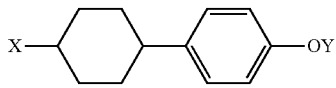

Chemical Formula 9
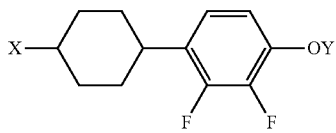

Chemical Formula 10
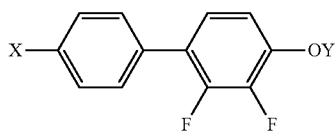

Chemical Formula 11
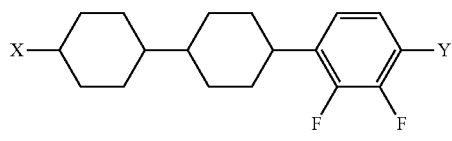

Chemical Formula 12
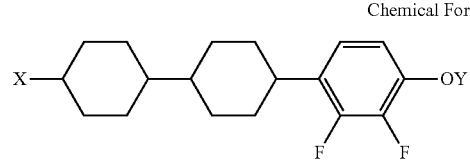

Chemical Formula 13
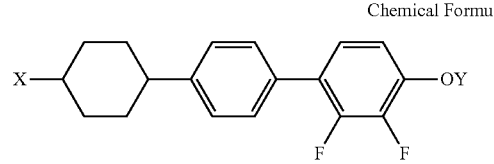

Chemical Formula 14
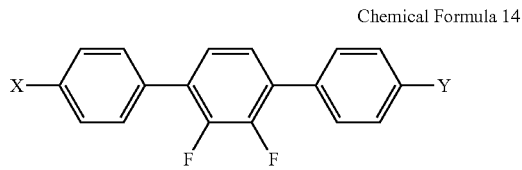

Chemical Formula 15
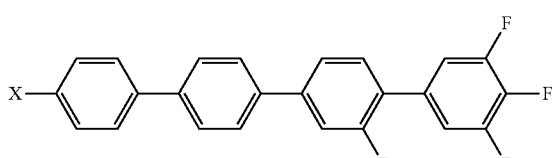

Chemical Formula 16
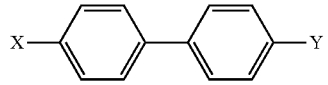

Chemical Formula 17
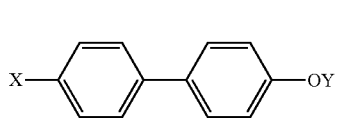

Chemical Formula 18
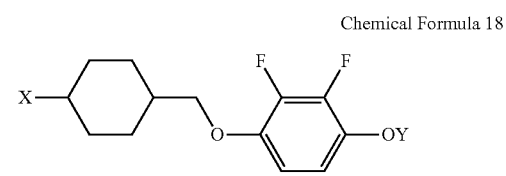

Chemical Formula 19
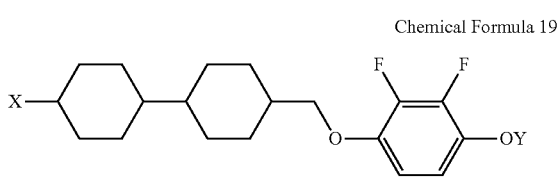

Chemical Formula 20
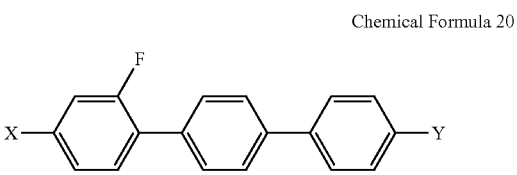

In Chemical Formula 2 to Chemical Formula 20, X and Y are groups represented by $C_nH_{2n+1}$, and n is 1 to 5.

In the entire liquid crystal composition, the content (amount) of the compounds represented by Chemical Formula 2 to Chemical Formula 20 are independently about 1 wt % to 30 wt % based on 100 wt % of the liquid crystal composition.

Specifically, the content of the compound represented by Chemical Formula 2 is in a range of about 10 wt % to about 30 wt % based on 100 wt % of the liquid crystal composition.

The content of the compound represented by Chemical Formula 3 is in a range of about 5 wt % to about 15 wt % based on 100 wt % of the liquid crystal composition. The content of the compound represented by Chemical Formula 4 is in a range of about 3 wt % to about 10 wt % based on 100 wt % of the liquid crystal composition. The content of the compound represented by Chemical Formula 5 is in a range of about 10 wt % to about 35 wt % based on 100 wt % of the liquid crystal composition. The content of the compound represented by Chemical Formula 6 is in a range of about 5 wt % to about 15 wt % based on 100 wt % of the liquid crystal composition. The content of the compound represented by Chemical Formula 7 is in a range of about 5 wt % to about 15 wt % based on 100 wt % of the liquid crystal composition. The content of the compound represented by Chemical Formula 8 is in a range of about 3 wt % to about 25 wt % based on 100 wt % of the liquid crystal composition. The content of the compound represented by Chemical Formula 9 is in a range of about 5 wt % to about 25 wt % based on 100 wt % of the liquid crystal composition. The content of the compound represented by Chemical Formula 10 is in a range of about 5 wt % to about 20 wt % based on 100 wt % of the liquid crystal composition. The content of the compound represented by Chemical Formula 11 is in a range of about 5 wt % to about 20 wt % based on 100 wt % of the liquid crystal composition. The content of the compound represented by Chemical Formula 12 is in a range of about 5 wt % to about 25 wt % based on 100 wt % embodiment may be in a range of −2.8 to −5.5. Also, rotation viscosity γ1 of liquid crystal composition according to an exemplary embodiment may be in a range of 70 millipascal seconds (mPa·s) to 140 mPa·s.

That is, the liquid crystal composition according to an exemplary embodiment, including the compound in which the cyclohexane is connected by double bond instead of the compound in which the cyclohexane is connected by single bond, has excellent properties.

Also, the liquid crystal composition according to an exemplary embodiment may include reactive mesogen.

Conventionally known materials can be used as a reactive mesogen, and the reactive mesogen can improve the control of the liquid crystal.

As stated above, the liquid crystal composition according to an exemplary embodiment includes the compound represented by Chemical Formula 1.

Chemical Formula 1

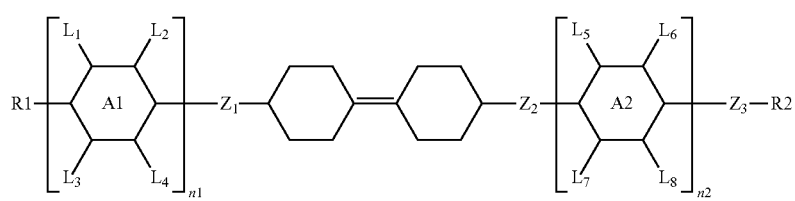

of the liquid crystal composition. The content of the compound represented by Chemical Formula 13 is in a range of about 5 wt % to about 25 wt % based on 100 wt % of the liquid crystal composition. The content of the compound represented by Chemical Formula 14 is in a range of about 1 wt % to about 15 wt % based on 100 wt % of the liquid crystal composition. The content of the compound represented by Chemical Formula 15 is in a range of about 0.03 wt % to about 5 wt % based on 100 wt % of the liquid crystal composition. The content of the compound represented by Chemical Formula 16 is in a range of about 5 wt % to about 15 wt % based on 100 wt % of the liquid crystal composition. The content of the compound represented by Chemical Formula 17 is in a range of about 5 wt % to about 10 wt % based on 100 wt % of the liquid crystal composition. The content of the compound represented by Chemical Formula 18 is in a range of about 8 wt % to about 16 wt % based on 100 wt % of the liquid crystal composition. The content of the compound represented by Chemical Formula 19 is in a range of about 10 wt % to about 35 wt % based on 100 wt % of the liquid crystal composition. The content of the compound represented by Chemical Formula 20 is in a range of about 1 wt % to about 10 wt % based on 100 wt % of the liquid crystal composition.

A refractive anisotropy Δn of the liquid crystal composition according to an exemplary embodiment may be in a range of 0.08 to 0.12. Also, the dielectric anisotropy Δ∈ of liquid crystal composition according to an exemplary The compound represented by Chemical Formula 1 includes the cyclohexane connected by double bond. The double bond positioned between two cyclohexane rings is blocked by an adjacent hydrogen atom, and therefore the reactivity of the double bond is not high and the double bond can be stable.

Also, another ring structure can be connected to the edge of the cyclohexane, and therefore the rotation viscosity or dielectric constant can be controlled according to the purpose of the liquid crystal.

Hereinafter, the physical properties of the liquid crystal composition according to the Comparative Example and the liquid crystal composition according to an exemplary embodiment will be compared.

The liquid crystal composition according to Comparative Example includes the compound in which two cyclohexane rings are connected by a single bond.

However, the liquid crystal composition according to an exemplary embodiment includes the compound in which two cyclohexane rings are connected by a double bond (the compound represented by Chemical Formula 1), and compared to the conventional liquid crystal composition, low temperature stability is improved and low viscosity is realized, thereby improving response speed.

Table 1 shows a compound composition and a content of the liquid crystal composition according to an exemplary embodiment.

TABLE 1
| No. | Liquid crystal molecule | Content (%) |
| --- | --- | --- |
| 1 | 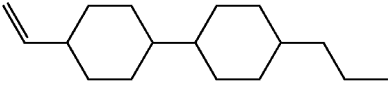 | 20 |
| 2 | 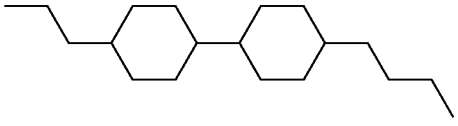 | 15 |
| 3 | 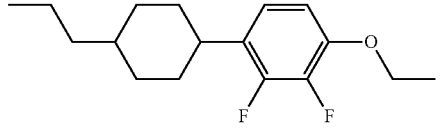 [SMILES: CCCC1CCC(c2ccc(OCC)c(F)c2F)CC1] | 20 |
| 4 | 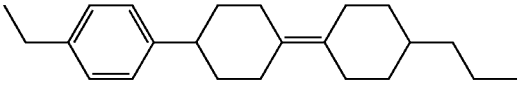 | 5 |
| 5 | 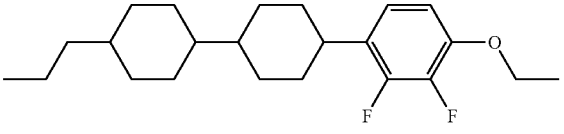 [SMILES: CCCC1CCC(C2CCC(c3ccc(OCC)c(F)c3F)CC2)CC1] | 15 |
| 6 | 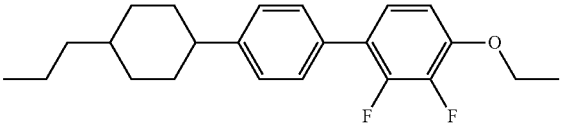 | 10 |
| 7 | 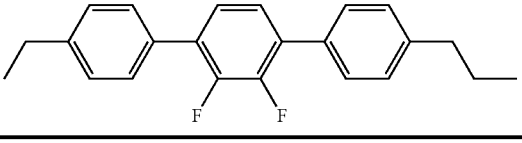 | 15 |
Table 2 shows a compound composition and a content of the liquid crystal composition according to the Comparative Example.
TABLE 2
| No. | Liquid crystal molecule | Content (%) |
| --- | --- | --- |
| 1 | 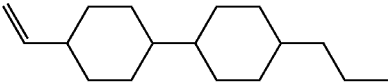 | 20 |
| 2 | 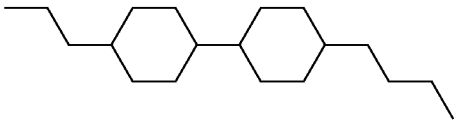 [SMILES: CCCCC1CCC(C2CCC(CCC)CC2)CC1] | 15 |
| 3 | 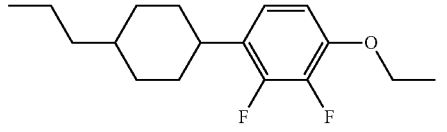 [SMILES: CCCC1CCC(c2ccc(OCC)c(F)c2F)CC1] | 20 |
| 4 | 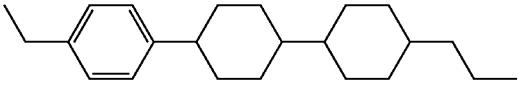 | 5 |

TABLE 2-continued

| No. | Liquid crystal molecule | Content (%) |
|---|---|---|
| 5 | 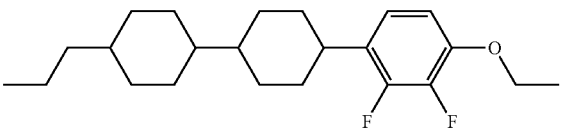 | 15 |
| 6 | 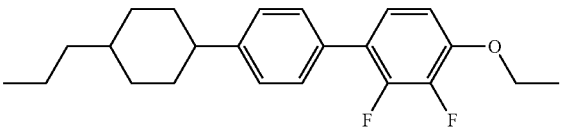 | 10 |
| 7 | 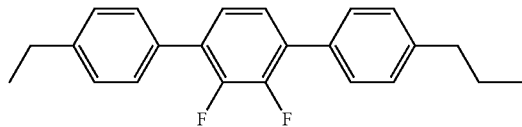 [SMILES: CCCc1ccc(-c2ccc(-c3ccc(CC)cc3)c(F)c2F)cc1] | 15 |

Table 3 compares the physical properties of the liquid crystal composition (exemplary embodiment 1) according to an exemplary embodiment having the composition of Table 1 and the liquid crystal composition (Comparative Example 1) according to the Comparative Example having the composition of Table 2.

In this case, the compared physical properties that are measured include a refractive anisotropy (Δn), a dielectric anisotropy (Δ∈), a rotation viscosity (γ1), a low temperature stability (LTS), and a voltage holding rate (VHR).

TABLE 3

| Properties | Δn | Δ∈ | γ1 (mPa · s) | LTS (low temperature stability at −30° C.) | VHR (UV 10J) |
|---|---|---|---|---|---|
| Exemplary embodiment 1 | 0.104 | −3.1 | 87 | Good | 88.3% |
| Comparative Example 1 | 0.104 | −3.1 | 89 | No Good | 88.6% |

Referring to Table 3, it can be confirmed that the liquid crystal composition according to an exemplary embodiment is equal to or better than the liquid crystal composition according to the Comparative Example with respect to all measured physical properties.

In particular, in the liquid crystal composition according to an exemplary embodiment, it can be confirmed that the low temperature stability is significantly improved compared to the liquid crystal composition according to the Comparative Example, as the basic properties, including the refractive anisotropy (Δn) and dielectric anisotropy (Δ∈), are not changed much.

While not wishing to be bound by theory, it is understood that the above improvement in properties is a result that the double bond is present between two cyclohexane rings in the cyclohexane combined compound (compound No. 4 of Table 1), while the single bond is present between two cyclohexane rings in the cyclohexane combined compound (compound No. 4 of Table 2) of the Comparative Example.

That is, in the case of the conventional liquid crystal composition of the Comparative Example, the cyclohexane rings are connected with a single bond (compound No. 4 of Table 2). In this case, the low temperature stability of the compound is low, and therefore, when the liquid crystal composition is included in excess, since the low temperature stability is decreased, a sufficient amount may not be included in the liquid crystal composition.

However, in the liquid crystal composition according to an exemplary embodiment, the cyclohexane rings are connected with a double bond (compound No. 4 of Table 1). This compound has excellent low temperature stability, and therefore, the compound may be included in the liquid crystal composition in excess.

Table 4 shows a compound composition and a content of the liquid crystal composition according to an exemplary embodiment. The composition of Table 4 includes the polar compound (compound No. 4 of Table 4) as a compound of Chemical Formula 1.

TABLE 4

| No. | Liquid crystal molecule | Content (%) |
|---|---|---|
| 1 | 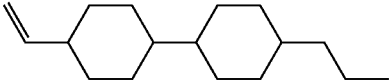 | 20 |
| 2 | 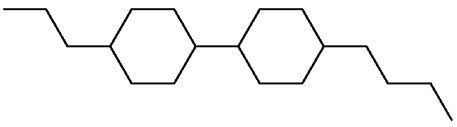 | 15 |

TABLE 4-continued

| No. | Liquid crystal molecule | Content (%) |
|---|---|---|
| 3 | | 20 |
| 4 | | 20 |
| 5 | | 10 |
| 6 | | 15 |

Table 5 shows a compound composition and a content of the liquid crystal composition according to the Comparative Example.

Table 6 compares the physical properties of the liquid crystal composition according to an exemplary embodiment (exemplary embodiment 2) having the composition of Table

TABLE 5

| No. | Liquid crystal molecule | Content (%) |
|---|---|---|
| 1 | | 20 |
| 2 | | 15 |
| 3 | | 20 |
| 4 | | 20 |
| 5 | | 10 |
| 6 | | 15 |

4 and the liquid crystal composition according to the Comparative Example (Comparative Example 2) having the composition of Table 5.

In this case, the compared physical properties that are measured include a refractive anisotropy (Δn), a dielectric anisotropy (Δ∈), a rotation viscosity (γ1), a low temperature stability (LTS), and a voltage holding rate (VHR).

TABLE 6

| Properties | Δn | Δ∈ | γ1 (mPa·s) | LTS (low temperature stability) at −30° C.) | VHR (UV 10J) |
|---|---|---|---|---|---|
| Exemplary embodiment 1 | 0.105 | −3.2 | 85 | Good | 88.5% |
| Comparative Example 1 | 0.104 | −3.1 | 87 | No Good | 88.7% |

Referring to Table 6, it can be confirmed that the liquid crystal composition according to exemplary embodiment 2 is equal to or better than the liquid crystal composition according to Comparative Example 2 with respect to all measured physical properties. In particular, in the liquid crystal composition according to exemplary embodiment 2, it may be confirmed that the low temperature stability is significantly improved compared to the liquid crystal composition according to the Comparative Example 2.

Next, a liquid crystal display including with the liquid crystal composition according to an exemplary embodiment will be described.

However, the structure of the described liquid crystal display is only one example and the liquid crystal display according to an exemplary embodiment may be clearly used without being limited to the case of a vertical alignment (VA) mode liquid crystal display.

First, an arrangement and a driving method of a signal line and a pixel of the liquid crystal display will be described with reference to FIG. 1. FIG. 1 is an equivalent circuit diagram for one pixel of a liquid crystal display according to an exemplary embodiment. That is, FIG. 1 is an equivalent circuit diagram of the display device of FIG. 2 to FIG. 4.

Referring to FIG. 1, one pixel PX of the liquid crystal display according to the present exemplary embodiment includes: a plurality of signal lines, including a gate line GL for transferring a gate signal, a data line DL for transferring a data signal, and a voltage division reference voltage line RL for transferring a voltage division reference voltage; first, second, and third switching elements Qa, Qb, and Qc; and, first and second liquid crystal capacitors Clca and Clcb connected to the plurality of signal lines.

The first and second switching elements Qa and Qb are connected to the gate line GL and the data line DL, respectively, and the third switching element Qc is connected to the output terminal of the second switching element Qb and the voltage division reference voltage line RL.

The first switching element Qa and the second switching element Qb are three-terminal elements, such as a thin film transistor, control terminals thereof are connected to the gate line GL, input terminals thereof are connected to the data line DL, an output terminal of the first switching element Qa is connected to a first liquid crystal capacitor Clca, and an output terminal of the second switching element Qb is connected to a second liquid crystal capacitor Clcb and an input terminal of the third switching element Qc.

The third switching element Qc is also a three-terminal element, such as a thin film transistor, and a control terminal thereof is connected to the gate line GL, the input terminal thereof is connected to the second liquid crystal capacitor Clcb, and an output terminal thereof is connected to the voltage division reference voltage line RL.

When a gate-on signal is applied to the gate line GL, the first switching element Qa, the second switching element Qb, and the third switching element Qc connected to the gate line GL are turned on. Accordingly, a data voltage applied to the data line DL is applied to a first subpixel electrode PEa and a second subpixel electrode PEb through the turned-on first switching element Qa and second switching element Qb. In this case, the data voltages applied to the first subpixel electrode PEa and the second subpixel electrode PEb are the same, and the first liquid crystal capacitor Clca and the second liquid crystal capacitor Clcb are charged to the same value as the difference between the common voltage and the data voltage. Similarly, the voltage charged in the second liquid crystal capacitor Clcb is divided through the turned-on third switching element Qc. Accordingly, the voltage value charged in the second liquid crystal capacitor Clcb is decreased by the difference between the common voltage and the voltage division reference voltage. That is, the voltage charged in the first liquid crystal capacitor Clca is higher than a voltage charged in the second liquid crystal capacitor Clcb.

As described above, the voltage charged in the first liquid crystal capacitor Clca and the voltage charged in the second liquid crystal capacitor Clcb become different from each other. Since the voltage of the first liquid crystal capacitor Clca and the voltage of the second liquid crystal capacitor Clcb are different from each other, inclination angles of liquid crystal molecules in the first subpixel and the second subpixel become different from each other, and thus luminance of the two subpixels becomes different from each other. Accordingly, when the voltage of the first liquid crystal capacitor Clca and the voltage of the second liquid crystal capacitor Clcb are appropriately adjusted, an image viewed from the side may be as close as possible to an image viewed from the front, thereby improving side visibility.

In the illustrated exemplary embodiment, in order to make the voltage charged in the first liquid crystal capacitor Clca and the voltage charged in the second liquid crystal capacitor Clcb different from each other, the liquid crystal display includes the third switching element Qc connected to the second liquid crystal capacitor Clcb and the voltage division reference voltage line RL, but in the case of a liquid crystal display according to another exemplary embodiment, the second liquid crystal capacitor Clcb may be connected to a step-down capacitor. In particular, the liquid crystal display includes the third switching element Qc including a first terminal connected to a step-down gate line, a second terminal connected to the second liquid crystal capacitor Clcb, and a third terminal connected to the step-down capacitor, and a part of the charge amount charged in the second liquid crystal capacitor Clcb is charged in the step-down capacitor, so that the charging voltages between the first liquid crystal capacitor Clcb and the second liquid crystal capacitor Clcb may be set differently. Further, in the case of a liquid crystal display according to another exemplary embodiment, the first liquid crystal capacitor Clca and the second liquid crystal capacitor Clcb are connected to different data lines and receive different data voltages, Thus, the charging voltages between the first liquid crystal capacitor Clca and the second liquid crystal capacitor Clcb may be set differently. In addition, the charging voltages between the first liquid crystal capacitor Clca and the second liquid crystal capacitor Clcb may be set differently by various other methods.

Next, the arrangement of the lower display panel and upper display panel according to the liquid crystal display will be described with reference to FIG. 2 to FIG. 4.

Figure 2:
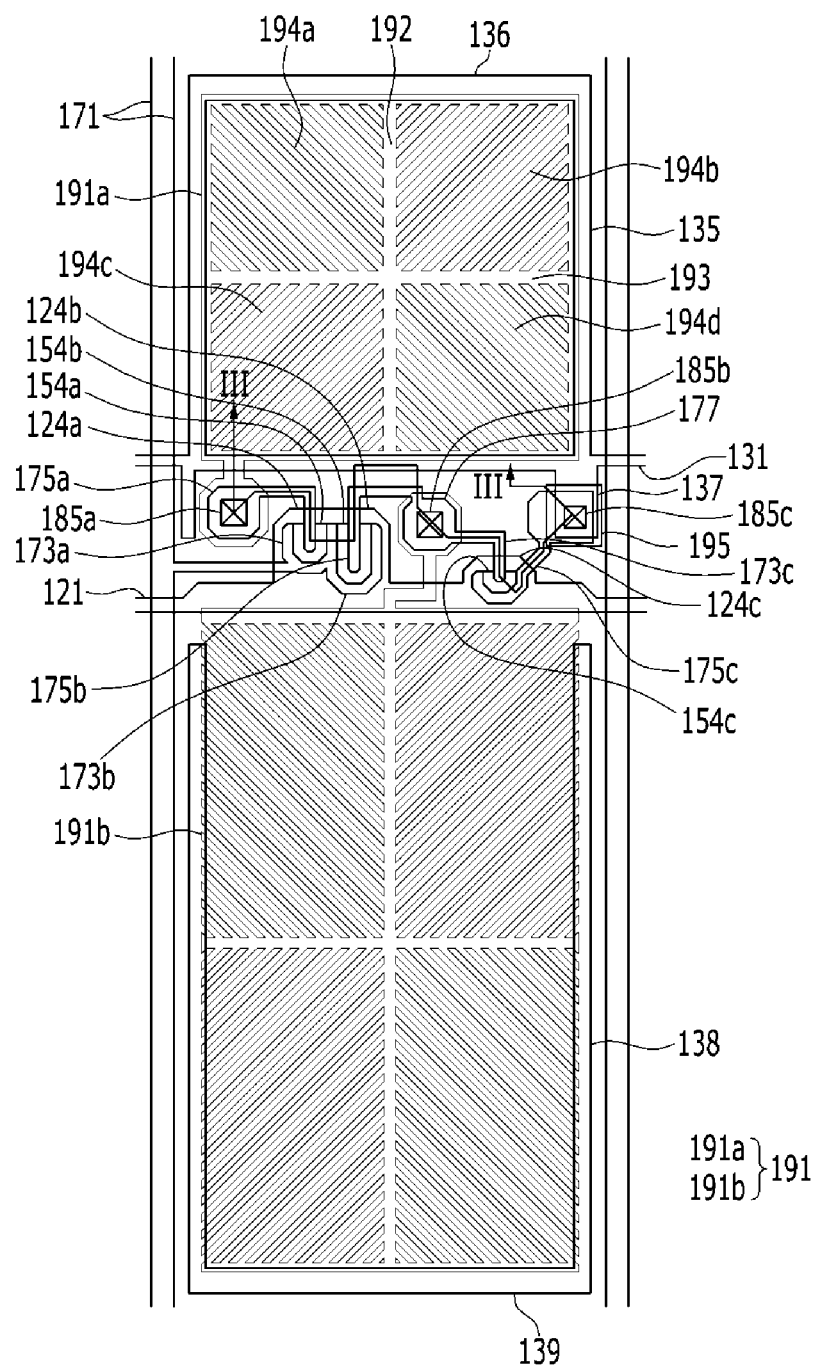
FIG. 2 is a layout view illustrating a display device according to an exemplary embodiment.
Figure 3:
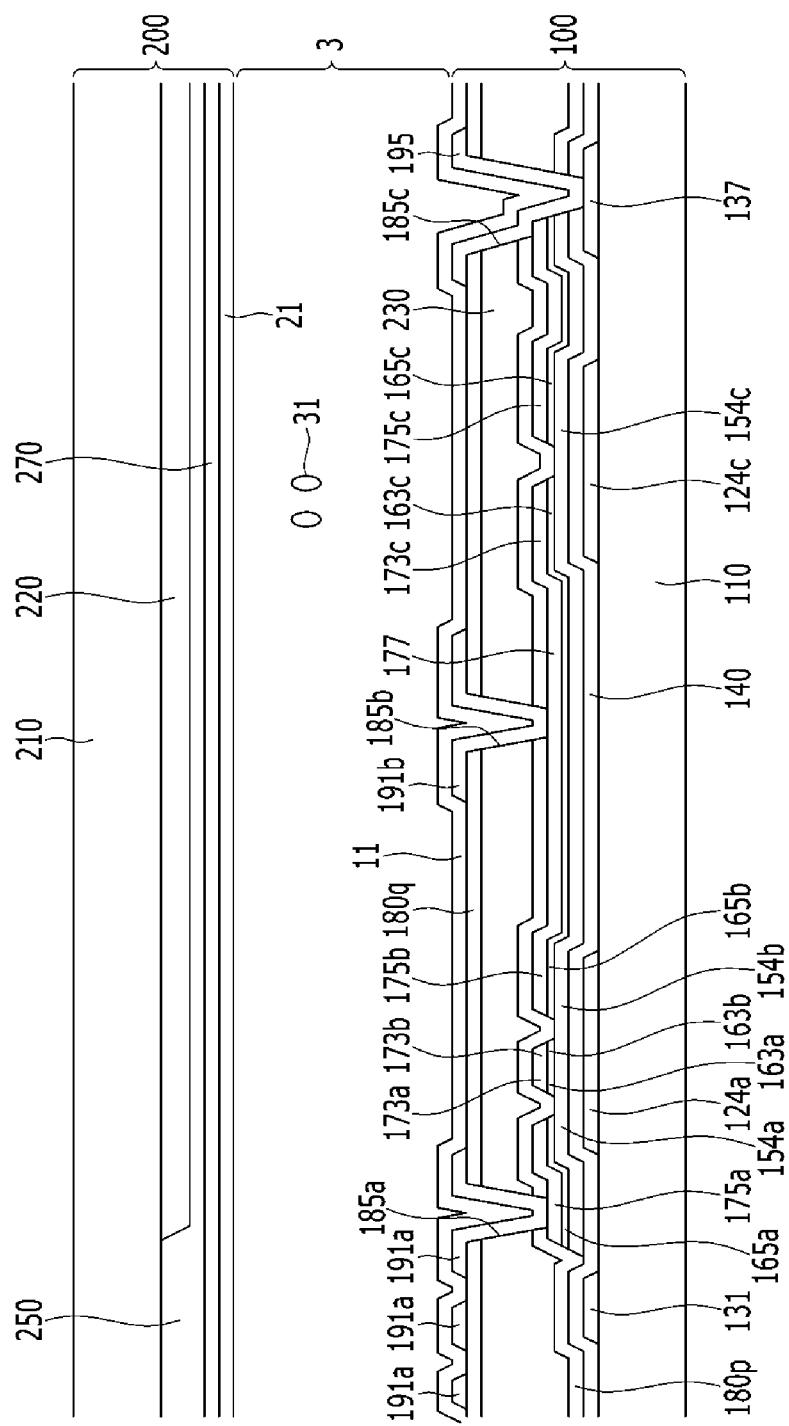
FIG. 3 is a cross-sectional view illustrating the display device taken along line III-III according to the exemplary embodiment illustrated in FIG. 2.

FIG. 2 is a layout view of a liquid crystal display according to an exemplary embodiment, and FIG. 3 is a cross-sectional view of the liquid crystal display of FIG. 2 taken along line III-III. FIG. 4 is a top plan view of a basic region of a pixel electrode of a lower panel according to an exemplary embodiment.

First, the lower display panel 100 will be described.

A gate conductor including a gate line 121 and a voltage division reference voltage line 131 is formed on an insulating substrate 110 formed of transparent glass, plastic, or the like.

The gate line 121 includes a first gate electrode 124a, a second gate electrode 124b, a third gate electrode 124c, and a wide end portion (not illustrated) for connection to another layer or an external driving circuit.

The voltage division reference voltage line 131 includes first storage electrodes 135 and 136, and a reference electrode 137. Second storage electrodes 138 and 139, which are not connected to the voltage division reference voltage line 131, but which overlap the second subpixel electrode 191b, are positioned on the lower panel 100.

A gate insulating layer 140 is formed on the gate line 121 and the voltage division reference voltage line 131.

A first semiconductor 154a, a second semiconductor 154b, and a third semiconductor 154c are formed on the gate insulating layer 140.

A plurality of ohmic contacts 163a, 165a, 163b, 165b, 163c, and 165c are formed on the semiconductors 154a, 154b, and 154c.

A plurality of data lines 171, including a first source electrode 173a and a second source electrode 173b, and data conductors including a first drain electrode 175a, a second drain electrode 175b, a third source electrode 173c, and a third drain electrode 175c are formed on the ohmic contacts 163a, 165a, 163b, 165b, 163c, and 165c, and the gate insulating layer 140.

The data conductors, as well as the semiconductors and the ohmic contacts positioned under the data conductors, may be simultaneously formed by using one mask.

The data line 171 includes a wide end portion (not illustrated) for connection with another layer or an external driving circuit.

The first gate electrode 124a, the first source electrode 173a, and the first drain electrode 175a form a first thin film transistor Qa together with the first semiconductor 154a, and a channel of the thin film transistor is formed on the semiconductor 154a between the first source electrode 173a and the first drain electrode 175a. Similarly, the second gate electrode 124b, the second source electrode 173b, and the second drain electrode 175b form a second thin film transistor Qb together with the second semiconductor 154b, and a channel of the thin film transistor is formed on the semiconductor 154b between the second source electrode 173b and the second drain electrode 175b; and the third gate electrode 124c, the third source electrode 173c, and the third drain electrode 175c form a third thin film transistor Qc together with the third semiconductor 154c, and a channel of the thin film transistor is formed on the semiconductor 154c between the third source electrode 173c and the third drain electrode 175c.

The second drain electrode 175b is connected with the third source electrode 173c, and includes a wide extended portion 177.

A first passivation layer 180p is formed on the data conductors 171, 173c, 175a, 175b, and 175c and exposed portions of the semiconductors 154a, 154b, and 154c. The first passivation layer 180p may include an inorganic insulating layer, such as a silicon nitride or a silicon oxide. The first passivation layer 180p may prevent a pigment of a color filter 230 from flowing into the exposed portions of the semiconductors 154a, 154b, and 154c.

The color filter 230 is formed on the first passivation layer 180p. The color filter 230 extends in a vertical direction along two adjacent data lines. A first light blocking member 220 is positioned on the first passivation layer 180p, an edge of the color filter 230, and the data line 171.

However, the color filter 230 may not be formed on the lower display panel 100, but on the upper display panel 200.

A second passivation layer 180q is formed on the color filter 230.

The second passivation layer 180q may include an inorganic insulating layer such as a silicon nitride or a silicon oxide. The second passivation layer 180q prevents lifting of the color filter 230 and reduces contamination of the liquid crystal layer 3 from organic material such as a solvent flowing from the color filter 230, thereby preventing defects such as afterimage, which may be generated when a screen is driven.

A first contact hole 185a and a second contact hole 185b that expose the first drain electrode 175a and the second drain electrode 175b are formed in the first passivation layer 180p and the second passivation layer 180q.

A third contact hole 185c that exposes a portion of the reference electrode 137 and a portion of the third drain electrode 175c is formed in the first passivation layer 180p, the second passivation layer 180q, and the gate insulating layer 140, and the third contact hole 185c is covered by a connecting member 195. The connecting member 195 electrically connects the reference electrode 137 and the third drain electrode 175c exposed through the third contact hole 185c.

A plurality of pixel electrodes 191 is formed on the second passivation layer 180q. Each of the pixel electrodes 191 includes a first sub-pixel electrode 191a and a second sub-pixel electrode 191b that are spaced apart from each other with the gate line 121 included therebetween, and are adjacent to each other in a column direction with respect to the gate line 121. The pixel electrodes 191 may be formed of a transparent material such as indium tin oxide (ITO), indium zinc oxide (IZO), or the like. The pixel electrodes 191 may be formed of a transparent conductive material such as ITO or IZO or the like, or a reflective metal such as aluminum, silver, chromium, or an alloy thereof.

Figure 4:
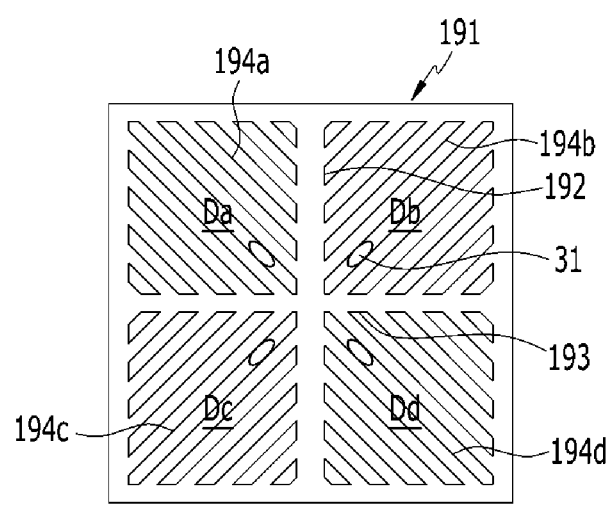
FIG. 4 is a top plan view illustrating a basic region of a pixel electrode of the liquid crystal display according to the exemplary embodiment.

The first sub-pixel electrode 191a and the second sub-pixel electrode 191b each include a basic electrode illustrated in FIG. 4 or at least one electrode modified based on the basic electrode.

The first sub-pixel electrode 191a and the second sub-pixel electrode 191b are respectively physically and electrically connected to the first drain electrode 175a and the second drain electrode 175b via the first contact hole 185a and the second contact hole 185b, and receive a data voltage from the first drain electrode 175a and the second drain electrode 175b. Here, a portion of the data voltage applied to the second drain electrode 175b is divided by the third source electrode 173c so that a voltage applied to the first sub-pixel electrode 191a is greater than a voltage applied to the second sub-pixel electrode 191b.

The first sub-pixel electrode 191a and the second sub-pixel electrode 191b, to which the data voltage is applied, generate an electrical field with the common electrode 270 of the upper display panel 200 so as to determine a direction of liquid crystal molecules of the liquid crystal layer 3 between the two electrodes 191 and 270. Luminance of light that passes through the liquid crystal layer 3 is varied according to a direction of liquid crystal molecules that is determined as described above.

The liquid crystal layer 3 will be described later in detail.

A lower alignment layer 11 is formed on the pixel electrode 191.

Next, a basic electrode will be described with reference to FIG. 4. Referring to FIG. 2 to FIG. 4, the first sub-pixel electrode 191a and the second sub-pixel electrode 191b each includes one basic electrode. For example, the basic electrode is illustrated based on the first sub-pixel electrode 191a in FIG. 4, but the basic electrode is modified based on the second-pixel electrode 191b.

As shown in FIG. 4, the overall shape of the basic electrode is a quadrangle, and includes a cross-shaped stem having a transverse stem 193 and a longitudinal stem 192 that cross. Further, the basic electrode is divided into a first subregion Da, a second subregion Db, a third subregion Dc, and a fourth subregion Dd by the horizontal stem portion 193 and the vertical stem portion 192, and each of the subregions Da to Dd respectively includes a plurality of first fine branch portions 194a, a plurality of second fine branch portions 194b, a plurality of third fine branch portions 194c, and a plurality of fourth fine branch portions 194d.

The first fine branch portions 194a extend obliquely in an upper left direction from the horizontal stem portion 193 or the vertical stem portion 192, and the second fine branch portions 194b extend obliquely in an upper right direction from the horizontal stem portion 193 or the vertical stem portion 192. Further, the third fine branch portions 194c extend in a lower left direction from the horizontal stem portion 193 or the vertical stem portion 192, and the fourth fine branch portions 194d extend obliquely in a lower right direction from the horizontal stem portion 193 or the vertical stem portion 192.

The first to fourth fine branch portions 194a, 194b, 194c, and 194d form an angle of approximately 45° or 135° with gate lines 121a and 121b or the horizontal stem portion 193. Further, the fine branch portions 194a, 194b, 194c, and 194d of the two adjacent subregions Da, Db, Dc, and Dd may be orthogonal to each other.

Widths of the fine branch portions 194a, 194b, 194c, and 194d may be in the range of 2.5 to 5.0 micrometers (μm) and a gap between the adjacent fine branch portions 194a, 194b, 194c, and 194d in one of the subregions Da, Db, Dc, or Dd may be in the range of 2.5 to 5.0 μm.

According to another embodiment, the widths of the fine branch portions 194a, 194b, 194c, and 194d may be increased to be closer to the horizontal stem portion 193 or the vertical stem portion 192, and a difference between the widest portion and the narrowest portion in one of the fine branch portions 194a, 194b, 194c, or 194d may be in the range of 0.2 to 1.5 μm.

The first subpixel electrode 191a and the second subpixel electrode 191b are connected to the first drain electrode 175a and the second drain electrode 175b through the first contact hole 185a and the second contact hole 185b, respectively, and receive the data voltage from the first drain electrode 175a and the second drain electrode 175b, respectively. In this case, sides of the first to the fourth fine branch portions 194a, 194b, 194c, and 194d distort an electric field and make a horizontal component that determines an inclination direction of the liquid crystal molecules 31. The horizontal component of the electric field is substantially horizontal to the sides of the first to fourth fine branch portions 194a, 194b, 194c, and 194d. Accordingly, as illustrated in FIG. 4, the liquid crystal molecules 31 are inclined in a direction parallel to the longitudinal direction of the fine branch portions 194a, 194b, 194c, and 194d. Since one pixel electrode 191 includes four subregions Da to Dd, in which longitudinal directions of the fine branch portions 194a, 194b, 194c, and 194d are different from each other, the liquid crystal molecules 31 are inclined in about four directions, and four domains, in which the alignment directions of the liquid crystal molecules 31 are different from each other, are formed in the liquid crystal layer 3. As described above, when the inclination direction of the liquid crystal molecules is diversified, a reference viewing angle of the liquid crystal display is increased.

Hereinafter, the upper display panel 200 will be described.

Referring to FIG. 2 and FIG. 3, a black matrix 220 is formed on the insulation substrate 210. The black matrix 220 is formed on the upper display panel 220 to correspond to a region of the lower panel 100 in which the data lines are formed and a region in which transistors or the like are formed.

An overcoat layer 250 is formed on the black matrix 220. The overcoat layer 250 may be omitted.

The common electrode 270 is formed on the overcoat layer 250. An upper alignment layer 21 is formed on the common electrode 270.

The liquid crystal layer 3 is formed between the lower display panel 100 and the upper display panel 200. Now, the liquid crystal layer 3 of the liquid crystal composition according to an exemplary embodiment will be described.

Specifically, the liquid crystal layer according to an exemplary embodiment includes one or more kinds of the compound represented by Chemical Formula 1.

Chemical Formula 1

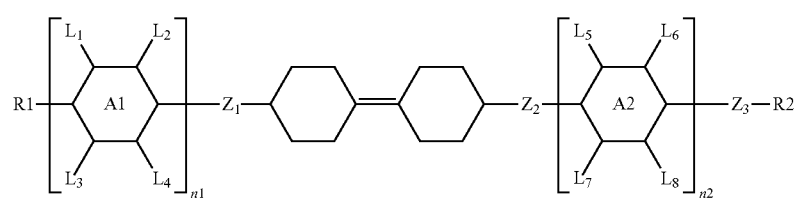

Wherein, in Chemical Formula 1,

and

are independently one or more selected from

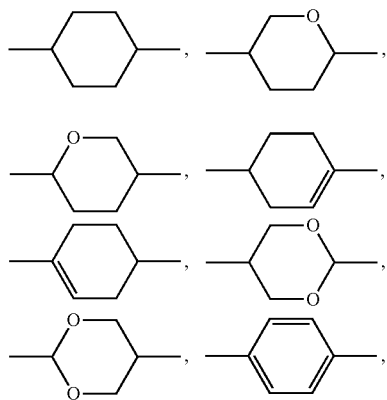

$L_1$ to $L_8$ are independently —H, —F, —Cl, —OCF$_3$, —CF$_3$, —CH$_2$F or —CHF$_2$, $Z_1$, $Z_2$ and $Z_3$ are independently a single bond, —COO—, —OCO—, —CF$_2$O—, —OCF$_2$—, —CH$_2$O, —OCH$_2$—, —SCH$_2$—, —CH$_2$S—, —CH$_2$CH$_2$—, —C$_2$F$_4$—, —CH$_2$CF$_2$—, —CF$_2$CH$_2$—, —(CH$_2$)$_z$— (wherein z is an integer of 0 to 10), —CH=CH—, —CF=CF—, —CH=CF—, —CF=CH—, —C≡C— or —CH=CHCH$_2$O—, R1 and R2 are independently hydrogen, halogen, cyano, a C1 to C5 alkyl, a C2 to C5 alkenyl, a C1 to C5 alkoxy, and $n_1$ and $n_2$ are independently integers of 0 to 3, provided that the sum of n1 and n2 is more than 1.

The description of liquid crystal composition is same as the above description, thus a detailed description of the same constituent elements is omitted here.

As such, in the liquid crystal display including the compound represented by Chemical Formula 1 as the liquid crystal layer, the rotation viscosity of the liquid crystal layer is low compared to the conventional liquid crystal display, thereby improving the response speed of the liquid crystal display.

The liquid crystal display according to the structure of FIG. 1 to FIG. 4 is only one example and the liquid crystal composition according to an exemplary embodiment may be clearly applied without being limited to the vertical alignment (VA) mode liquid crystal display in which the pixel electrode is positioned in the first display panel and the common electrode is positioned in the second display panel.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A liquid crystal composition comprising
one or more compounds represented by Chemical Formula 1:

Chemical Formula 1

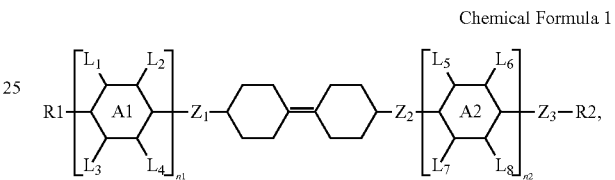

wherein, in Chemical Formula 1,

and

are independently one or more selected from,

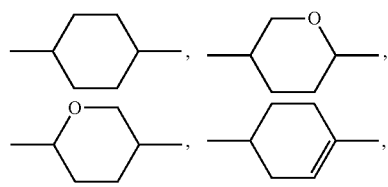

Chemical Formula 1

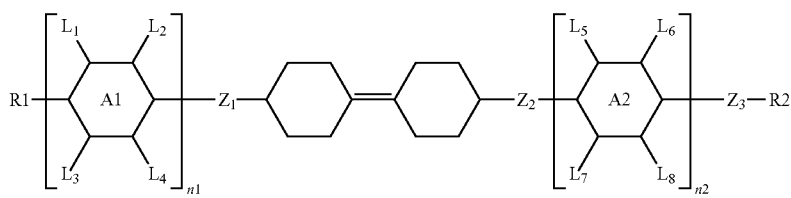

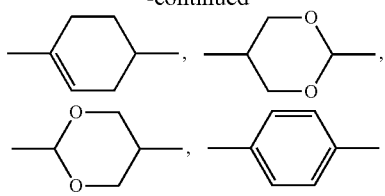

$L_1$ to $L_8$ are independently —H, —F, —Cl, —OCF$_3$, —CF$_3$, —CH$_2$F or —CHF$_2$, $Z_1$, $Z_2$ and $Z_3$ are independently a single bond, —COO—, —OCO—, —CF$_2$O—, —OCF$_2$—, —CH$_2$O, —OCH$_2$—, —SCH$_2$—, —CH$_2$S—, —CH$_2$CH$_2$—, —C$_2$F$_4$—, —CH$_2$—CF$_2$—, —CF$_2$CH$_2$—, —(CH$_2$)$_z$— (wherein z is an integer of 0 to 10), —CH═CH—, —CF═CF—, —CH═CF—, —CF═CH—, —C≡C— or —CH═CHCH$_2$O—, R1 and R2 are independently hydrogen, halogen, cyano, a C1 to C5 alkyl, a C2 to C5 alkenyl, or a C1 to C5 alkoxy, and $n_1$ and $n_2$ are independently integers of 0 to 3, provided the sum of n1 and n2 is more than 1.

2. The liquid crystal composition of claim 1, wherein:

in the compound represented by Chemical Formula 1,

R1 is a C1 to C5 alkyl and R2 is a C1 to C5 alkyl, or

R1 is a C1 to C5 alkyl and R2 is a C2 to C5 alkenyl, or

R1 is a C1 to C5 alkyl and R2 is a C1 to C5 alkoxy.

3. The liquid crystal composition of claim 1, wherein:

the compound represented by Chemical Formula 1 comprises one or more selected from compounds represented by Chemical Formula 1-1 to Chemical Formula 1-16:

Chemical Formula 1-1

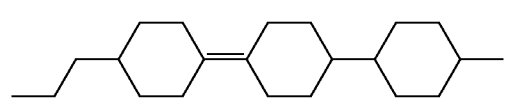

Chemical Formula 1-2

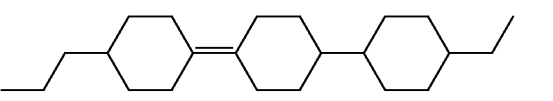

Chemical Formula 1-3

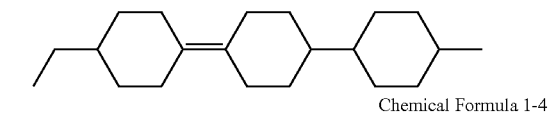

Chemical Formula 1-4

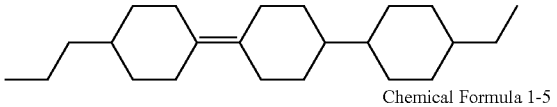

Chemical Formula 1-5

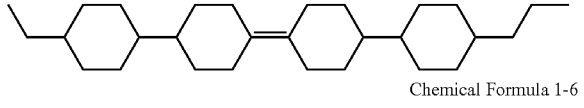

Chemical Formula 1-6

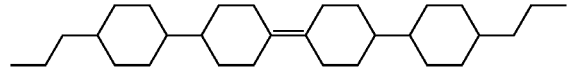

Chemical Formula 1-7

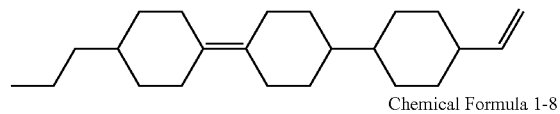

Chemical Formula 1-8

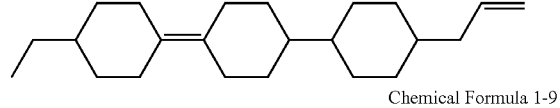

Chemical Formula 1-9

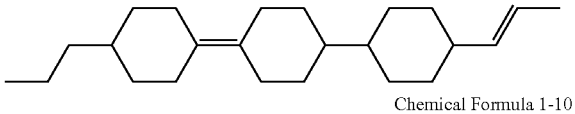

Chemical Formula 1-10

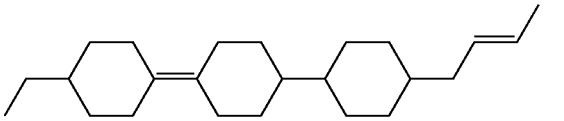

Chemical Formula 1-11

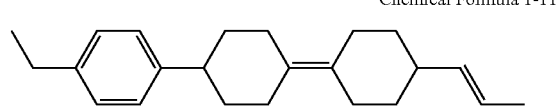

Chemical Formula 1-12

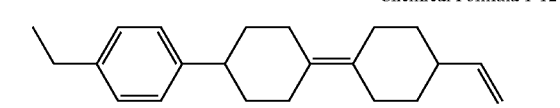

Chemical Formula 1-13

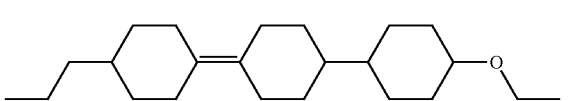

Chemical Formula 1-14

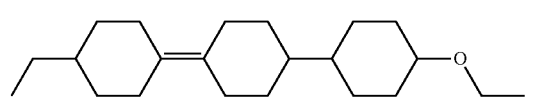

Chemical Formula 1-15

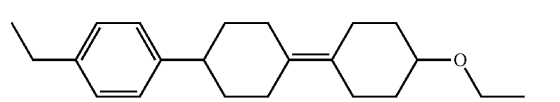

Chemical Formula 1-16

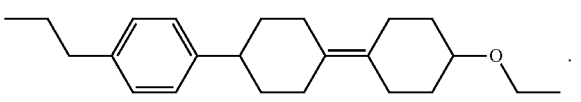

4. The liquid crystal composition of claim 1, wherein:

the compound represented by Chemical Formula 1 comprises one or more selected from compounds represented by Chemical Formula 1-17 to Chemical Formula 1-29:

Chemical Formula 1-17

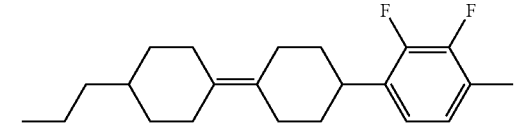

Chemical Formula 1-18
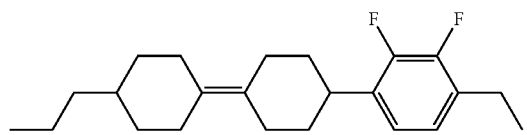

Chemical Formula 1-19
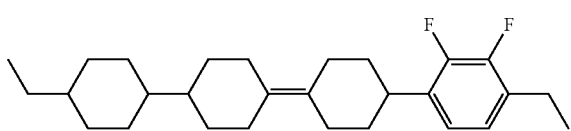

Chemical Formula 1-20
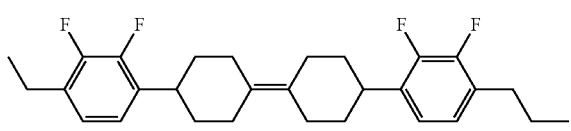

Chemical Formula 1-21
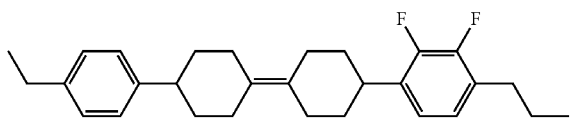

Chemical Formula 1-22
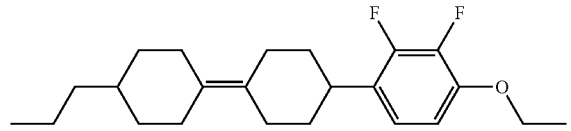

Chemical Formula 1-23
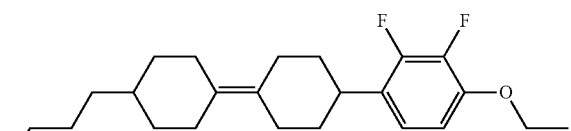

Chemical Formula 1-24
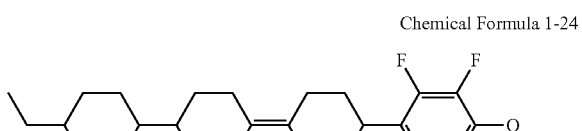

Chemical Formula 1-25
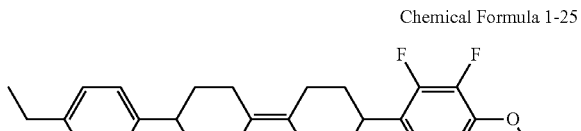

Chemical Formula 1-26
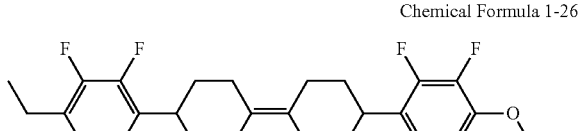

Chemical Formula 1-27
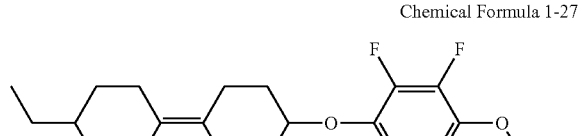

Chemical Formula 1-28
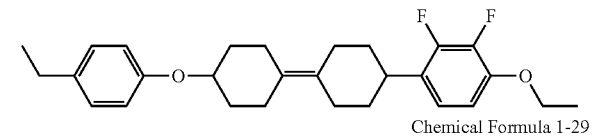

Chemical Formula 1-29
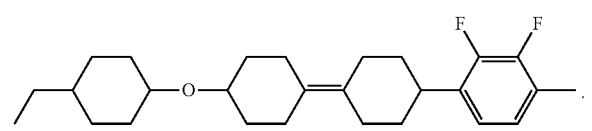

5. The liquid crystal composition of claim 1, wherein:
an amount of the compound represented by Chemical Formula 1 is in a range of about 0.1 percent by weight to about 60 percent by weight based on 100 percent by weight of the liquid crystal composition.

6. The liquid crystal composition of claim 1, wherein:
the liquid crystal composition comprises one or more compounds selected from Chemical Formula 2 to Chemical Formula 20:

Chemical Formula 2
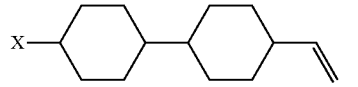

Chemical Formula 3
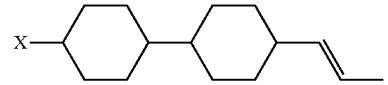

Chemical Formula 4
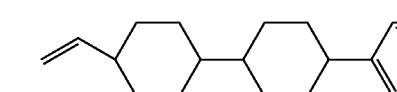

Chemical Formula 5
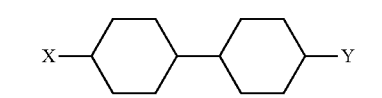

Chemical Formula 6
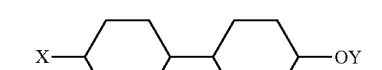

Chemical Formula 7
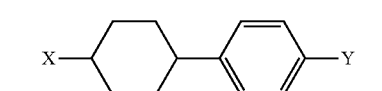

Chemical Formula 8
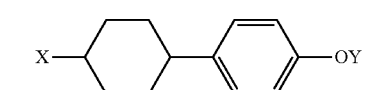

Chemical Formula 9
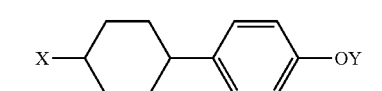

Chemical Formula 10
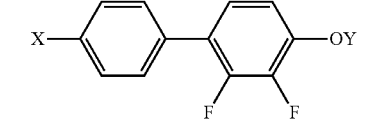

-continued

Chemical Formula 11
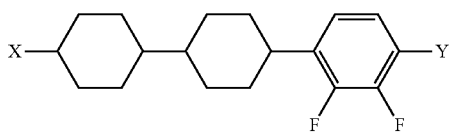

Chemical Formula 12
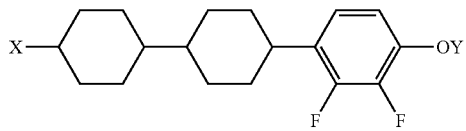

Chemical Formula 13
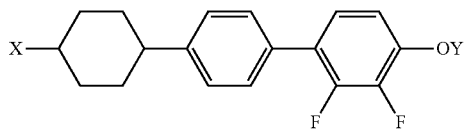

Chemical Formula 14
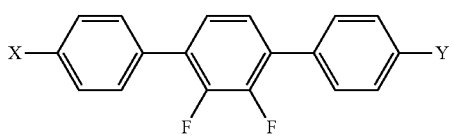

Chemical Formula 15
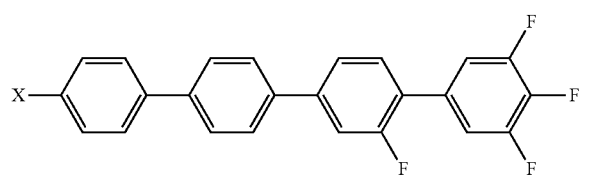

Chemical Formula 16
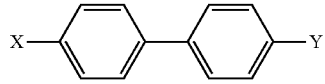

Chemical Formula 17
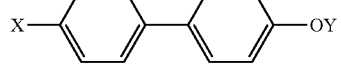

Chemical Formula 18
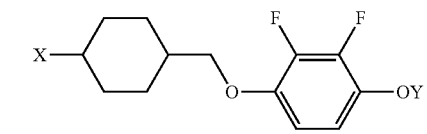

Chemical Formula 19
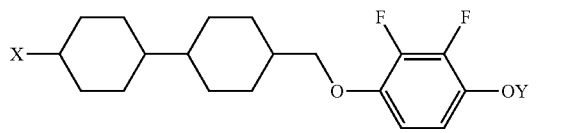

Chemical Formula 20
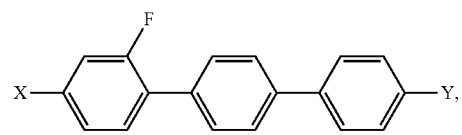

wherein, in Chemical Formula 2 to Chemical Formula 20, X and Y are independently $C_nH_{2n+1}$, wherein n is 1 to 5.

7. The liquid crystal composition of claim 6, wherein:
an amount of Chemical Formula 2 to Chemical Formula 20 is in a range of about 1 percent by weight to about 30 percent by weight based on 100 percent by weight of the liquid crystal composition.

8. The liquid crystal composition of claim 6, wherein:
the compound represented by Chemical Formula 1 is the compound represented by Chemical Formula 1-17, and
the liquid crystal composition comprises at least two of the compounds represented by Chemical Formula 31 to Chemical Formula 36:

Chemical Formula 1-17
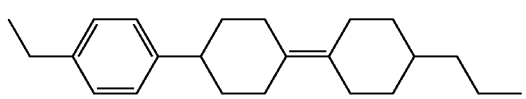

Chemical Formula 31
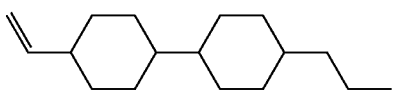

Chemical Formula 32
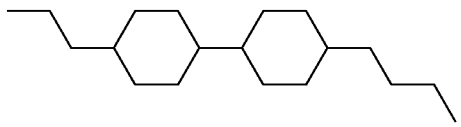 [SMILES: CCCCC1CCC(C2CCC(CCC)CC2)CC1]

Chemical Formula 33
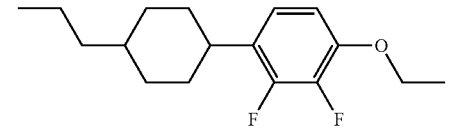

Chemical Formula 34
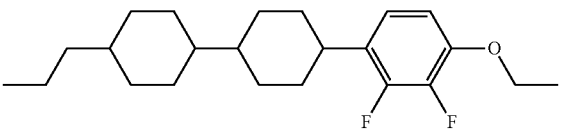 [SMILES: CCCC1CCC(C2CCC(c3ccc(OCC)c(F)c3F)CC2)CC1]

Chemical Formula 35
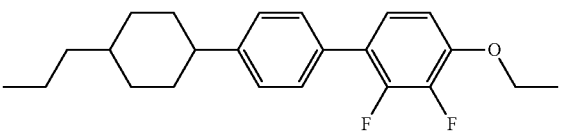 [SMILES: CCCC1CCC(c2ccc(-c3ccc(OCC)c(F)c3F)cc2)CC1]

Chemical Formula 36
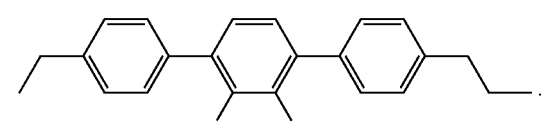

9. The liquid crystal composition of claim 6, wherein:
the compound represented by Chemical Formula 1 is the compound represented by Chemical Formula 1-18, and
the liquid crystal composition comprises at least two of the compounds represented by Chemical Formula 31 to Chemical Formula 33, Chemical Formula 35, and Chemical Formula 36:

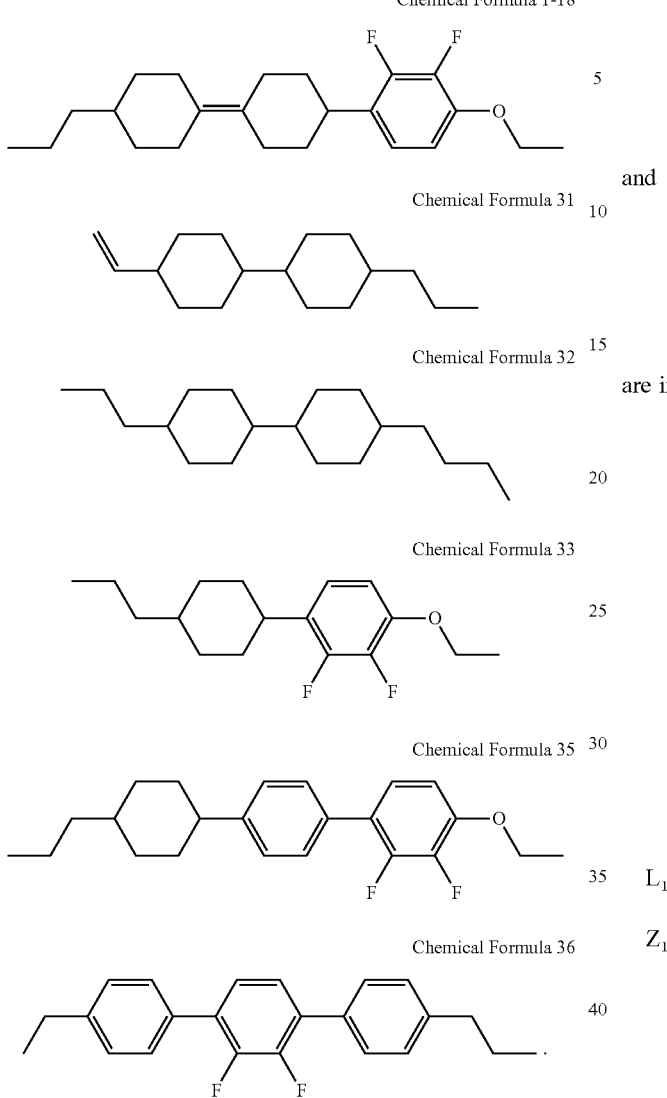

Chemical Formula 1-18

Chemical Formula 31

Chemical Formula 32

Chemical Formula 33

Chemical Formula 35

Chemical Formula 36

10. The liquid crystal composition of claim 1, wherein:
the liquid crystal composition further comprises a reactive mesogen.

11. A liquid crystal display comprising
pixel electrode disposed on a first insulation substrate,
a second insulation substrate configured to face the first insulation substrate, and
a liquid crystal layer disposed between the first insulation substrate and the second insulation substrate,
wherein the liquid crystal layer comprises a compound represented by Chemical Formula 1:

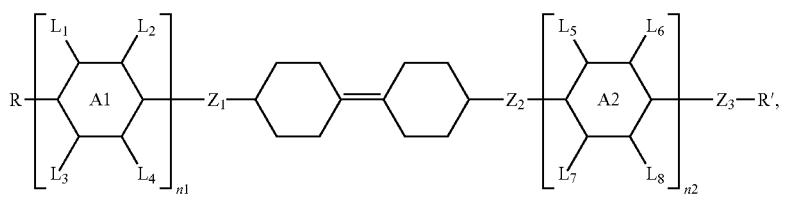

Chemical Formula 1 wherein, in Chemical Formula 1,

and

are independently one or more selected from,

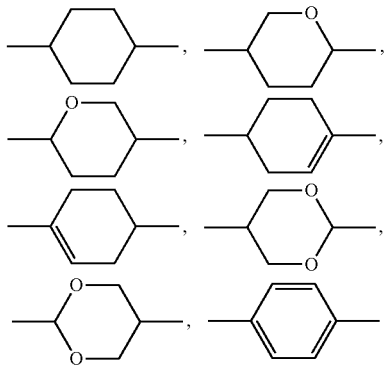

$L_1$ to $L_8$ are independently —H, —F, —Cl, —OCF$_3$, —CF$_3$, —CH$_2$F or —CHF$_2$, $Z_1$, $Z_2$ and $Z_3$ are independently a single bond, —COO—, —OCO—, —CF$_2$O—, —OCF$_2$—, —CH$_2$O, —OCH$_2$—, —SCH$_2$—, —CH$_2$S—, —CH$_2$CH$_2$—, —C$_2$F$_4$—, —CH$_2$—CF$_2$—, —CF$_2$CH$_2$—, —(CH$_2$)$_z$— (wherein z is an integer of 0 to 10), —CH=CH—, —CF=CF—, —CH=CF—, —CF=CH—, —C≡C— or —CH=CHCH$_2$O—, R1 and R2 are independently hydrogen, halogen, cyano, a C1 to C5 alkyl, a C2 to C5 alkenyl, a C1 to C5 alkoxy, and $n_1$ and $n_2$ are independently integers of 0 to 3, provided that the sum of $n_1$ and $n_2$ is more than 1.

12. The liquid crystal display of claim 11, wherein:
in the compound represented by Chemical Formula 1,
R1 is a C1 to C5 alkyl and R2 is a C1 to C5 alkyl, or
R1 is a C1 to C5 alkyl and R2 is a C2 to C5 alkenyl, or
R1 is a C1 to C5 alkyl and R2 is a C1 to C5 alkoxy.

13. The liquid crystal display of claim 11, wherein:

the compound represented by Chemical Formula 1 comprises one or more selected from compounds represented by Chemical Formula 1-1 to Chemical Formula 1-16:

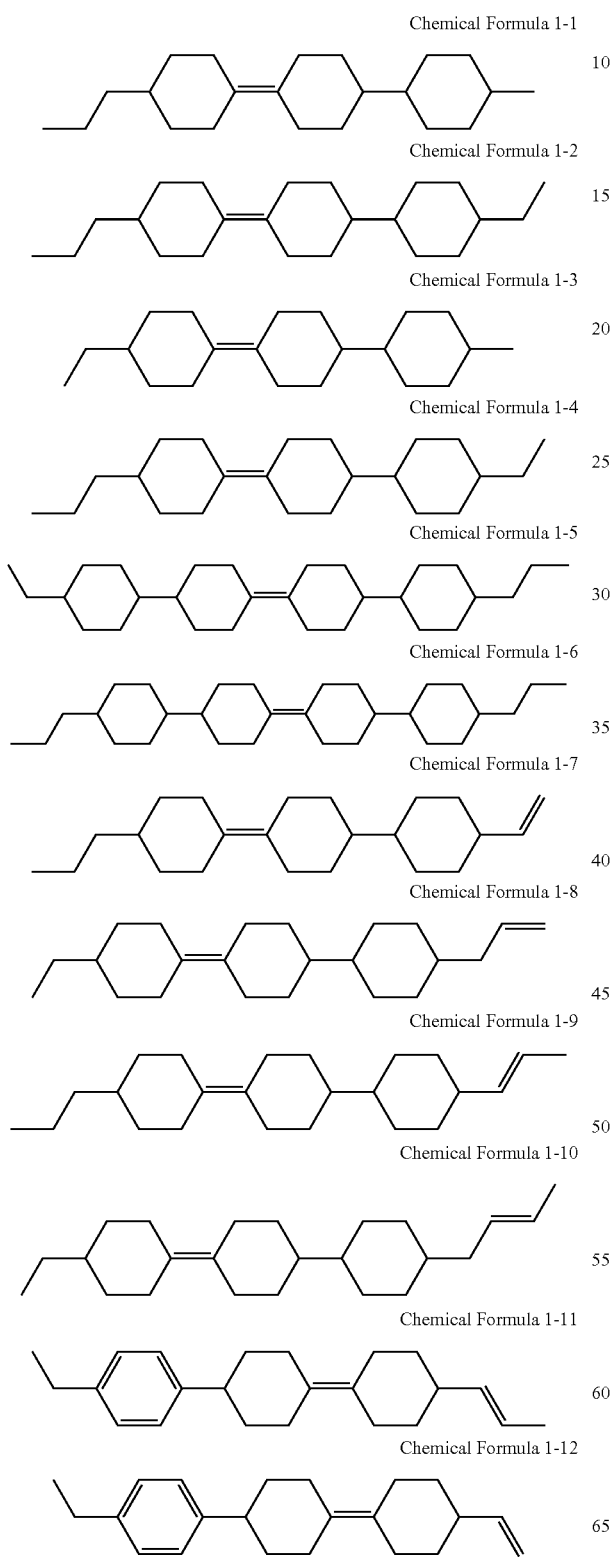

-continued

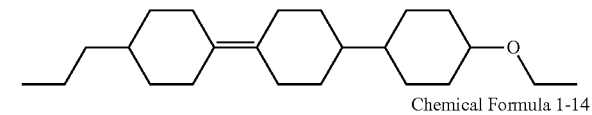

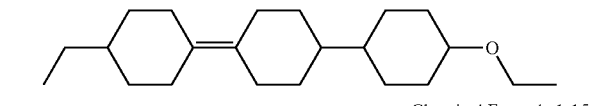

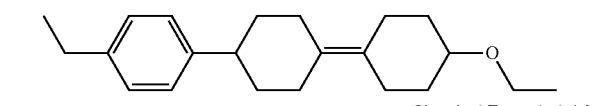

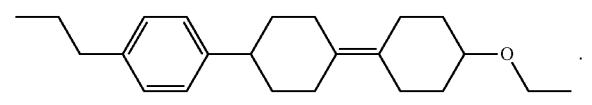

14. The liquid crystal display of claim 11, wherein:

the compound represented by Chemical Formula 1 comprises one or more selected from compounds represented by Chemical Formula 1-17 to Chemical Formula 1-29:

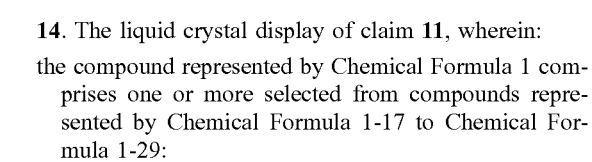

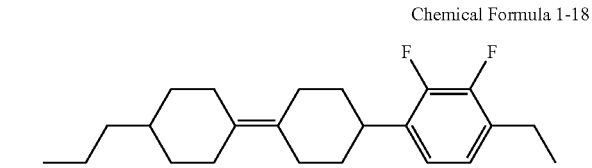

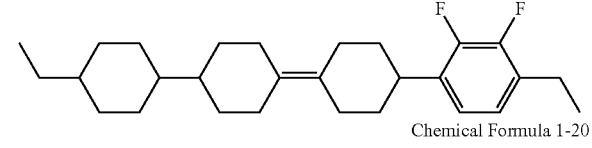

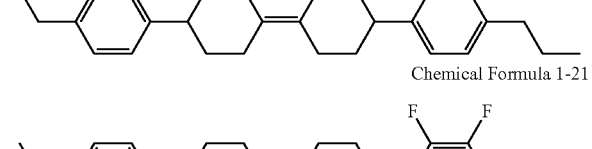

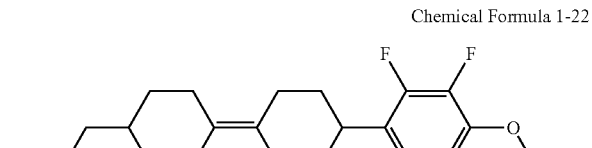

-continued

Chemical Formula 1-23
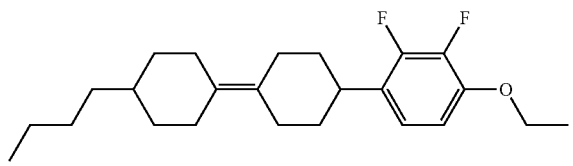

Chemical Formula 1-24
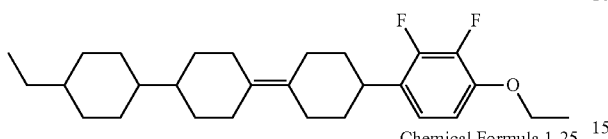

Chemical Formula 1-25
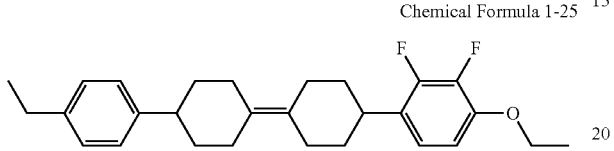

Chemical Formula 1-26
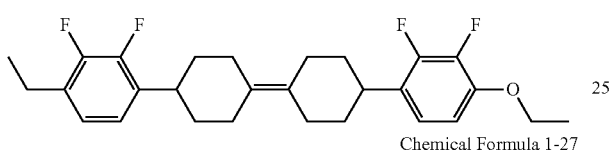

Chemical Formula 1-27
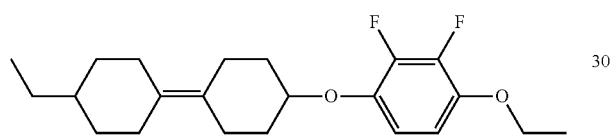

Chemical Formula 1-28
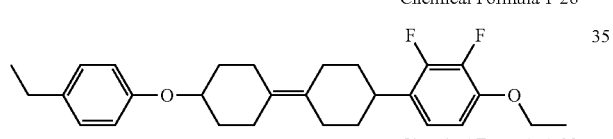

Chemical Formula 1-29
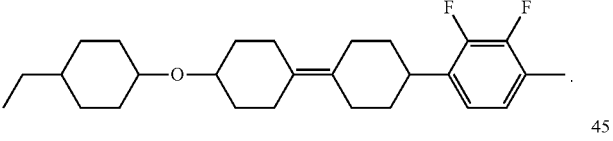

15. The liquid crystal display of claim 11, wherein:
an amount of the compound represented by Chemical Formula 1 is in a range of about 0.1 percent by weight to about 60 percent by weight based on 100 percent by weight of the liquid crystal layer.

16. The liquid crystal display of claim 11, wherein:
the liquid crystal layer comprises one or more compounds selected from Chemical Formula 2 to Chemical Formula 20:

Chemical Formula 2
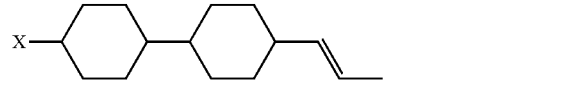

Chemical Formula 3

Chemical Formula 4
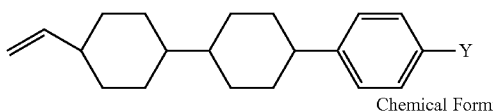

Chemical Formula 5
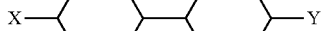

Chemical Formula 6

Chemical Formula 7
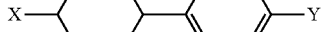

Chemical Formula 8

Chemical Formula 9
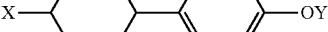

Chemical Formula 10
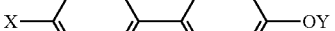

Chemical Formula 11
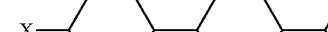

Chemical Formula 12

Chemical Formula 13

Chemical Formula 14
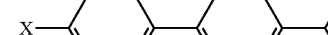

Chemical Formula 15

Chemical Formula 16

[Structure: X—phenyl—phenyl—Y]

Chemical Formula 17

[Structure: X—phenyl—phenyl—OY]

Chemical Formula 18

[Structure: X—cyclohexyl—CH₂—O—(difluorophenyl)—OY]

Chemical Formula 19

[Structure: X—cyclohexyl—cyclohexyl—CH₂—O—(difluorophenyl)—OY]

Chemical Formula 20

[Structure: X—(fluorophenyl)—phenyl—phenyl—Y]

wherein in Chemical Formula 2 to Chemical Formula 20, X and Y are independently $C_nH_{2n+1}$, wherein n is 1 to 5.

17. The liquid crystal display of claim 16, wherein:
an amount of Chemical Formula 2 to Chemical Formula 20 is in a range of about 1 percent by weight to about 30 percent by weight based on 100 percent by weight of the liquid crystal layer.

18. The liquid crystal display of claim 16, wherein:
the compound represented by Chemical Formula 1 is the compound represented by Chemical Formula 1-17, and
the liquid crystal layer comprises at least two of the compounds represented by Chemical Formula 31 to Chemical Formula 36:

Chemical Formula 1-17

[Structure]

Chemical Formula 31

[Structure]

Chemical Formula 32

[Structure]

Chemical Formula 33

[Structure]

Chemical Formula 34

[Structure]

Chemical Formula 35

[Structure]

Chemical Formula 36

[Structure]

19. The liquid crystal display of claim 16, wherein:
the compound represented by Chemical Formula 1 is the compound represented by Chemical Formula 18, and
the liquid crystal layer comprises at least two of the compounds represented by Chemical Formula 31 to Chemical Formula 33, Chemical Formula 35, and Chemical Formula 36:

Chemical Formula 1-18

[Structure]

Chemical Formula 31

[Structure]

Chemical Formula 32

[Structure]

Chemical Formula 33

[Structure]

-continued
Chemical Formula 35
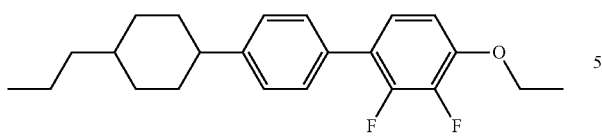
Chemical Formula 36
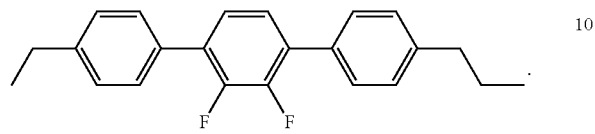
20. The liquid crystal display of claim 11, wherein:
the liquid crystal layer further comprises a reactive mesogen.
* * * * *